United States Patent
Basilion et al.

(10) Patent No.: US 12,133,901 B2
(45) Date of Patent: Nov. 5, 2024

(54) PSMA LIGAND TARGETED COMPOUNDS AND USES THEREOF

(71) Applicant: CASE WESTERN RESERVE UNIVERSITY, Cleveland, OH (US)

(72) Inventors: James Basilion, Cleveland, OH (US); Clemens Burda, Cleveland, OH (US); Dong Luo, Cleveland, OH (US); Xinning Wang, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 761 days.

(21) Appl. No.: 17/424,084

(22) PCT Filed: Jan. 21, 2020

(86) PCT No.: PCT/US2020/014460
§ 371 (c)(1),
(2) Date: Jul. 19, 2021

(87) PCT Pub. No.: WO2020/150740
PCT Pub. Date: Jul. 23, 2020

(65) Prior Publication Data
US 2022/0096663 A1    Mar. 31, 2022

Related U.S. Application Data

(60) Provisional application No. 62/794,251, filed on Jan. 18, 2019.

(51) Int. Cl.
| | |
|---|---|
| *A61K 49/04* | (2006.01) |
| *A61K 9/14* | (2006.01) |
| *A61K 33/242* | (2019.01) |
| *A61K 41/00* | (2020.01) |
| *A61K 47/54* | (2017.01) |
| *A61P 35/00* | (2006.01) |

(52) U.S. Cl.
CPC ............ *A61K 49/0423* (2013.01); *A61K 9/14* (2013.01); *A61K 33/242* (2019.01); *A61K 41/0038* (2013.01); *A61K 47/542* (2017.08); *A61P 35/00* (2018.01)

(58) Field of Classification Search
CPC .... A61K 49/0423; A61K 9/14; A61K 33/242; A61K 41/0038; A61K 47/542; A61P 35/00
See application file for complete search history.

(56) References Cited

U.S. PATENT DOCUMENTS

| | | | |
|---|---|---|---|
| 6,217,869 B1 | 4/2001 | Meyer et al. | |
| 9,439,966 B2 | 9/2016 | Karathanasis et al. | |
| 9,889,199 B2 | 2/2018 | Basilion et al. | |
| 10,207,005 B2 | 2/2019 | Basilion et al. | |
| 10,363,313 B2 | 7/2019 | Basilion et al. | |
| 10,709,794 B2 | 7/2020 | Basilion et al. | |
| 2002/0010351 A1 | 1/2002 | Serhan | |
| 2002/0103517 A1 | 8/2002 | West et al. | |
| 2002/0122806 A1 | 9/2002 | Chinnaiyan et al. | |
| 2003/0044805 A1 | 3/2003 | Mirkin et al. | |
| 2004/0077844 A1 | 4/2004 | Jacobson et al. | |
| 2005/0273143 A1 | 12/2005 | Kanzius et al. | |
| 2006/0083781 A1 | 4/2006 | Shastri et al. | |
| 2006/0088475 A1 | 4/2006 | Duimstra et al. | |
| 2006/0233712 A1 | 10/2006 | Penades et al. | |
| 2008/0193381 A1 | 8/2008 | Babich et al. | |
| 2009/0061010 A1 | 3/2009 | Zale et al. | |
| 2009/0181101 A1 | 7/2009 | Rademacher et al. | |
| 2009/0221764 A1 | 9/2009 | Shumaker-Parry et al. | |
| 2010/0324008 A1 | 12/2010 | Low et al. | |
| 2012/0323164 A1 | 12/2012 | Kenney et al. | |
| 2015/0366968 A1 | 12/2015 | Basilion et al. | |

FOREIGN PATENT DOCUMENTS

| | | |
|---|---|---|
| WO | 2004/037975 A2 | 5/2004 |
| WO | 2005/055982 A2 | 6/2005 |
| WO | 2005/099693 A2 | 10/2005 |
| WO | 2008/019052 A2 | 2/2008 |
| WO | 2008057437 A1 | 5/2008 |
| WO | 2011106639 A1 | 9/2011 |
| WO | 2012016713 A2 | 2/2012 |
| WO | 2014/127365 A1 | 8/2014 |

OTHER PUBLICATIONS

Applicant: Case Western Reserve University; PCT International Application No. PCT/US2020/014460; Filed Jan. 21, 2020; PCT International Search Report dated Apr. 6, 2020; 2 pgs.
Bonnet et al, AJNR Am. J. Neuroradiol., 2010, vol. 31, pp. 401-409.
Duimstra et al, J. Am. Chem. Soc., vol. 127, pp. 12847-12855 (Year: 2005).
EP Office action for Application No. 14751113.3-1109, dated Jan. 1, 2019.
Extended Search Report for Application No. 14751113.3-1453/ 2958596, dated Oct. 10, 2016.
Ikeda, Masato, et al, "Supramolecular hydrogel capsule showing prostate specific antigent-responsive function for ensing and targeting prostate cancer cells"; Chem. Sci., 2010, 1, 491-498.
Kularatne, Sumith A., et al., "Synthesis and Biological Analysis of Prostate-Specific Membrane Antigen-Targeted Anticancer Prodrugs"; Journal of Medicinal Chemistry, vol. 53, No. 21, Nov. 11, 2010, pp. 7767-7777, KP055103918.
Major et al, Acc. Chem. Res., 2009, vol. 42, No. 7, pp. 893-903.
Pedley et al, Methods in Molecular Science, 2004, vol. 90, pp. 491-514.
Urbanczyk-Pearson et al, Nature Protocols, vol. 3, No. 3, pp. 341-350 (Year: 2008).

(Continued)

*Primary Examiner* — Robert S Cabral
(74) *Attorney, Agent, or Firm* — Tarolli, Sundheim, Covell & Tummino LLP

(57) ABSTRACT

Prostate-specific membrane antigen (PSMA) targeted compounds having formula (I), nanoclusters formed thereof, pharmaceutical compositions comprising a plurality of these compounds, and methods for treating and detecting cancers in a subject are described herein.

24 Claims, 10 Drawing Sheets

(56) References Cited

OTHER PUBLICATIONS

U.S. Appl. No. 16/573,570, filed Sep. 17, 2019, U.S. Non-Final Rejection dated Jun. 10, 2022, 24 pgs.
U.S. Appl. No. 16/901,874, filed Jun. 15, 2020, U.S. Non-Final Rejection dated Aug. 18, 2022, 13 pgs.
Application No. 20741364.2 European Search Report dated May 4, 2023.

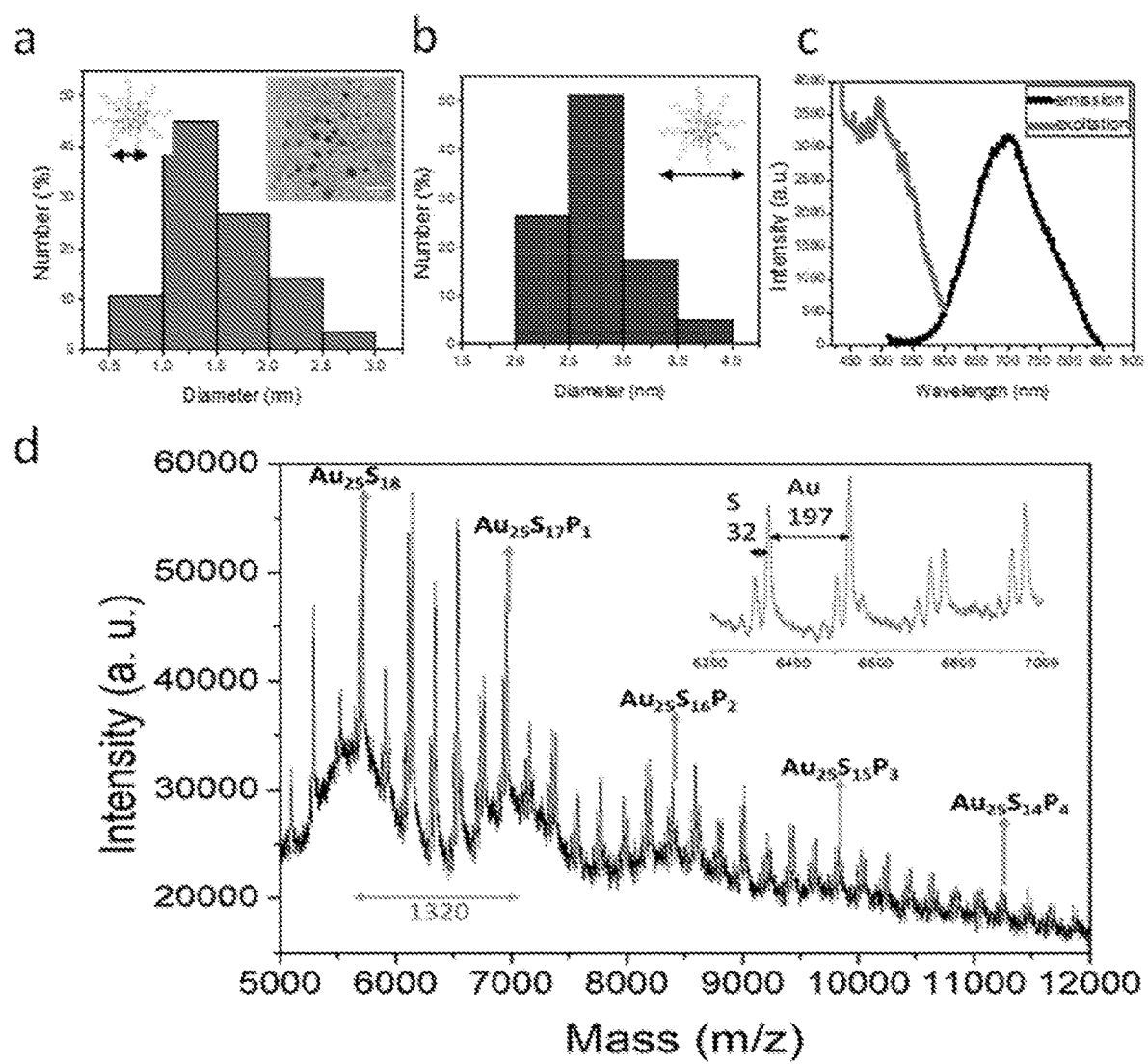
Fig. 2A-D

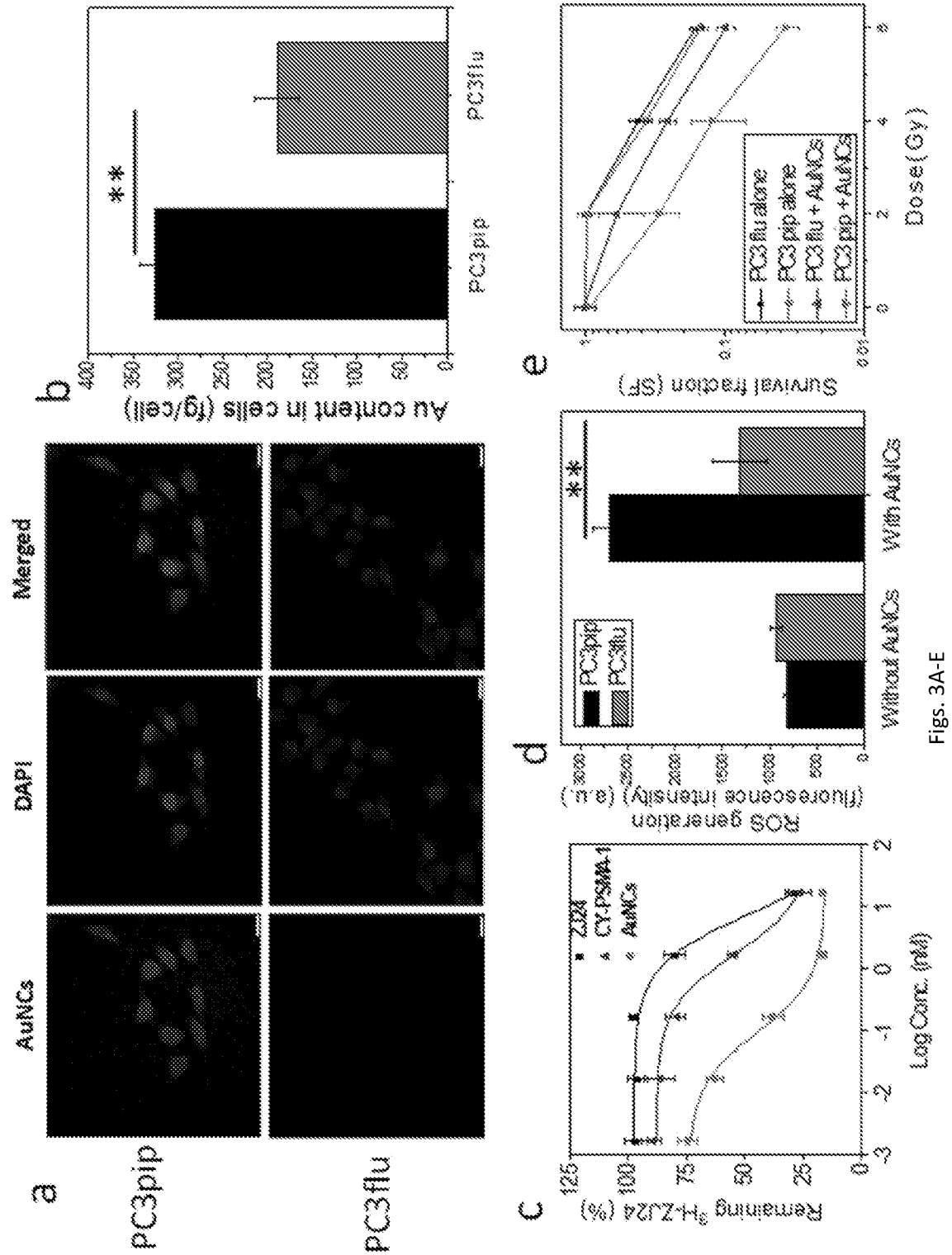
Figs. 3A-E

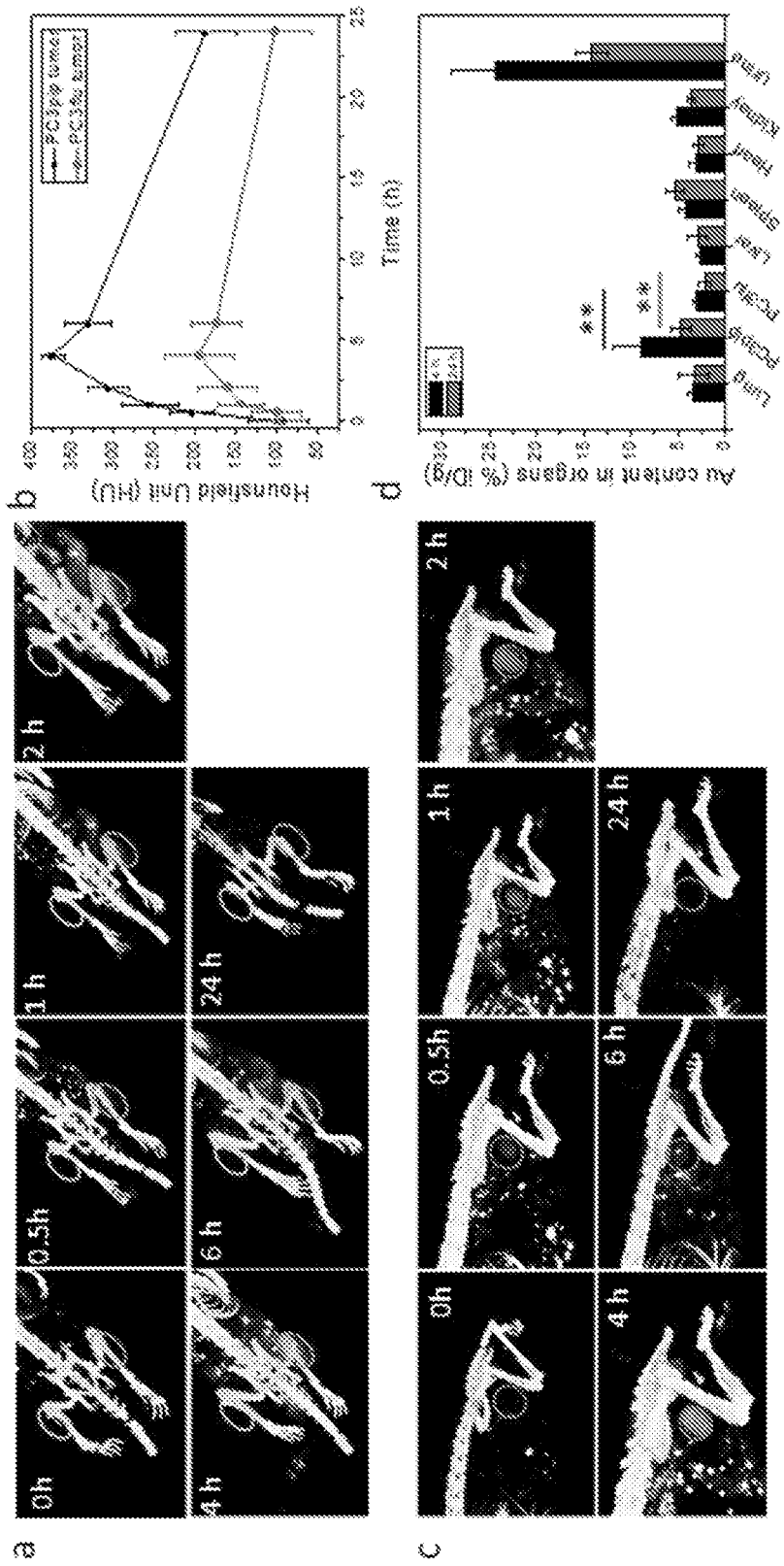
Fig. 4A-D

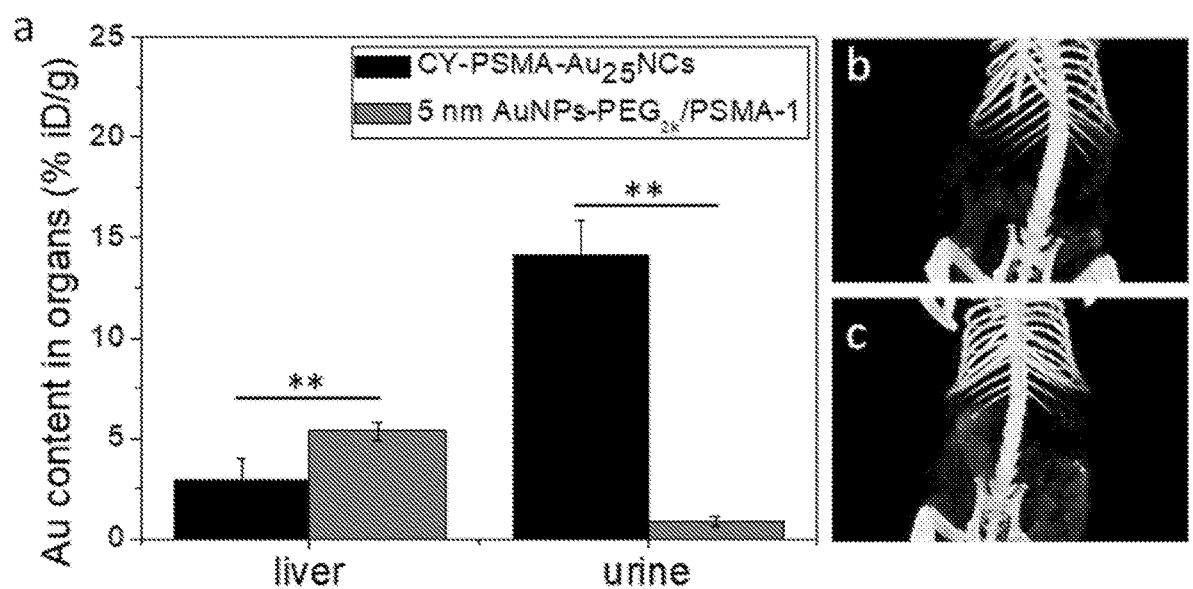
Fig. 5A-C

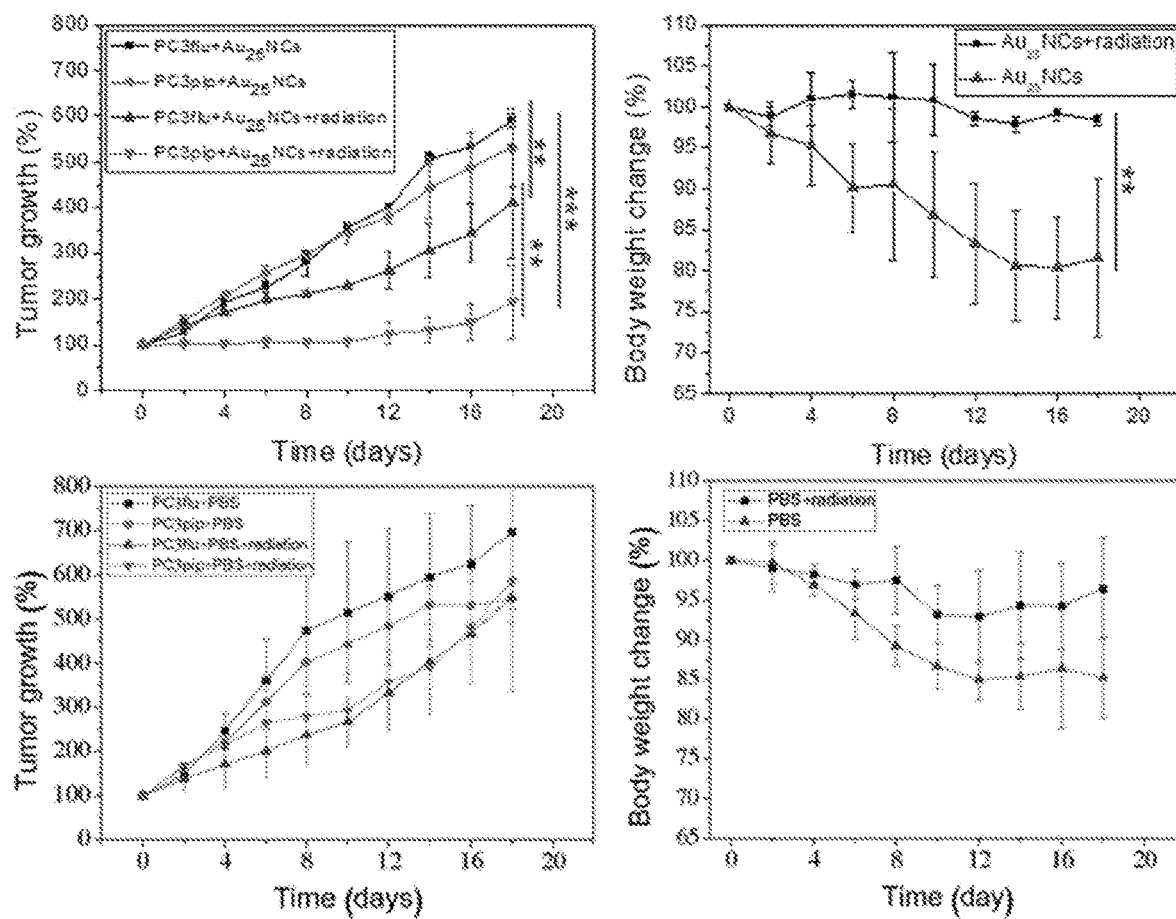
Figs. 6A-D

PSMA LIGAND TARGETED COMPOUNDS AND USES THEREOF

RELATED APPLICATION

This application claims priority from U.S. Provisional Application No. 62/794,251, filed Jan. 18, 2019, the subject matter of which is incorporated herein by reference in its entirety.

GOVERNMENT FUNDING

This invention was made with government support under Grant No. RO1EB020353-03 awarded by The National Institutes of Health (NIH). The United States government has certain rights in the invention.

TECHNICAL FIELD

This application relates to prostate-specific membrane antigen (PSMA) ligand targeted gold compounds, nanocluster aggregates thereof and to their use in compositions for targeting, imaging, and treating cancer.

BACKGROUND

Prostate cancer is the most diagnosed cancer among men in the United States. For treatment of prostate cancer, radical prostatectomies still remains the most direct and effective approach, however, when cancer has extended outside the prostate, surgery may be unable to remove all the malignant nodules, resulting in a high recurrence rate of cancer. In this case, radiation therapy, for instance, is necessary to reduce surgery-related morbidities. More than half of the patients receive radiation in the form of electrons, protons or photons (gamma- or X-rays) during their battle against cancers. However, in the practice of radiation treatment, normal tissues are also exposed and potential impairment is unavoidable. Even given recent advances, radiotherapy can still be hardly used alone for tumor eradication, especially when the tumor cells are radioresistant (e.g., hypoxic), underirradiated, or outside the targeted region.

Prostate-specific membrane antigen (PSMA) is a 120 kDa protein expressed in prostate tissues and was originally identified by reactivity with a monoclonal antibody designated 7E11-C5 (Horoszewicz et al., 1987, Anticancer Res. 7:927-935; U.S. Pat. No. 5,162,504). PSMA is characterized as a type II transmembrane protein sharing sequence identity with the transferrin receptor (Israeli et al., 1994, Cancer Res. 54:1807-1811). PSMA is a glutamate carboxy-peptidase that cleaves terminal carboxy glutamates from both the neuronal dipeptide N-acetylaspartylglutamate (NAAG) and gamma-linked folate polyglutamate. That is, expression of PSMA cDNA confers the activity of N-acetylated α-linked acidic dipeptidase or "NAALADase" activity (Carter et al., 1996, PNAS 93:749-753).

PSMA is expressed in increased amounts in prostate cancer, and elevated levels of PSMA are also detectable in the sera of these patients (Horoszewicz et al., 1987, supra; Rochon et al., 1994, Prostate 25:219-223; Murphy et al., 1995, Prostate 26:164-168; and Murphy et al., 1995, Anticancer Res. 15:1473-1479). As a prostate carcinoma marker, PSMA is believed to serve as a target for imaging and cytotoxic treatment modalities for prostate cancer. Prostate carcinogenesis, for example, is associated with an elevation in PSMA abundance and enzymatic activity of PSMA. PSMA antibodies, particularly indium-111 labeled and tritium labeled PSMA antibodies, have been described and examined clinically for the diagnosis and treatment of prostate cancer. PSMA is expressed in prostatic ductal epithelium and is present in seminal plasma, prostatic fluid and urine.

Recent evidence suggests that PSMA is also expressed in tumor associated neovasculature of a wide spectrum of malignant neoplasms including conventional (clear cell) renal carcinoma, transitional cell carcinoma of the urinary bladder, testicular embryonal carcinoma, colonic adenocarcinoma, neuroendocrine carcinoma, gliobastoma multiforme, malignant melanoma, pancreatic ductal carcinoma, non-small cell lung carcinoma, soft tissue carcinoma, breast carcinoma, and prostatic adenocarcinoma. (Chang et al. (1999) Cancer Res. 59, 3192-3198).

Gold has excellent radiation enhancing capability as it exhibits great mass energy absorption coefficients. Gold has also been shown to generate secondary radiation and emit high energy in the form of scattered photons, photoelectrons, Compton electrons, auger electrons, electro-positron pairs and fluorescence photons upon radiation, and induce free radicals and ionizations to kill cancer cells.

In the development of gold nanoparticle-based radiosensitizers, high tumor targeting and fast body clearance is the key, as an unnecessary over-exposure of radiation to healthy tissue and potential gold particle-induced toxicity are not desirable. There remains a need for an ideal radiosensitizer developed for cancer, such a prostate cancer.

SUMMARY

Embodiments described herein relate to PSMA ligand targeted gold compounds, nanocluster aggregates thereof, pharmaceutical compositions comprising these compounds, and methods for treating and detecting cancers (e.g., prostate cancer) in a subject using pharmaceutical compositions including a plurality of these compounds or nanoclusters thereof.

In some embodiments, the compound can include the formula (I):

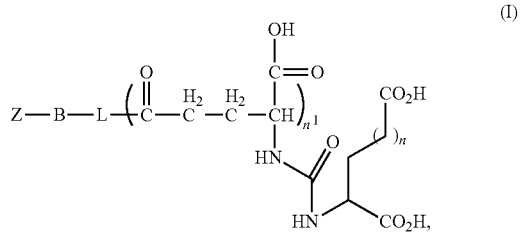

wherein:

n and $n^1$ are each independently 1, 2, 3, or 4;

L is an optionally substituted aliphatic or heteroaliphatic linking group;

B comprises at least one negatively charged amino acid; and

Z has the formula

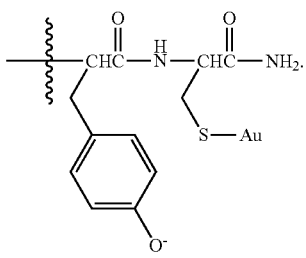

In some embodiments, L can include at least one ring selected from the group consisting of an optionally substituted 4 to 7 membered nonaromatic heterocyclic ring and an optionally substituted C4-C7 cycloalkyl ring.

In some embodiments, B has the following formula:

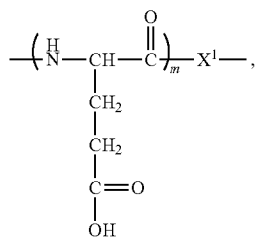

wherein m is 1, 2, 3, or 4, $X^1$ is an amino acid.

In other embodiments, B has the following formula:

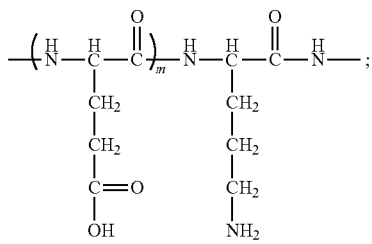

wherein m is 1, 2, 3, or 4.

In other embodiments, the compound can have the formula (II):

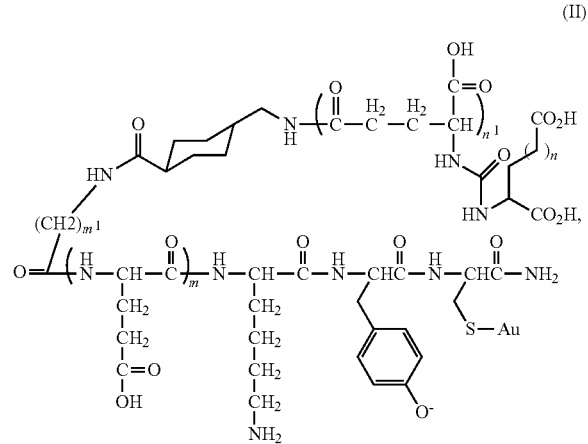

wherein m, n, and $n^1$ are each independently 1, 2, 3, or 4, and wherein $m^1$ is 3-7.

Other embodiments described herein relate to a composition for detecting and/or treating cancer, such as prostate cancer, in a subject. The composition can include a plurality of compounds that include the formula (I):

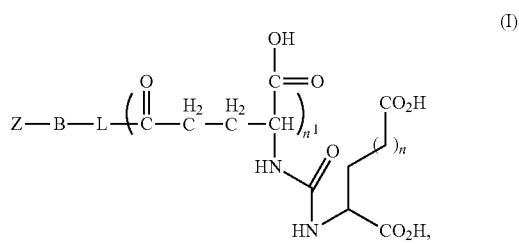

wherein:

n and $n^1$ are each independently 1, 2, 3, or 4;

L is an optionally substituted aliphatic or heteroaliphatic linking group;

B comprises at least one negatively charged amino acid; and

Z has the formula

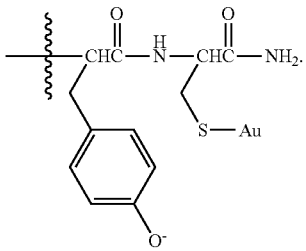

In some embodiments, L can include at least one ring selected from the group consisting of an optionally substituted 4 to 7 membered nonaromatic heterocyclic ring and an optionally substituted C4-C7 cycloalkyl ring.

In some embodiments, B has the following formula:

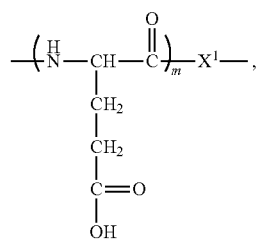

wherein m is 1, 2, 3, or 4, $X^1$ is an amino acid.

In other embodiments, B has the following formula:

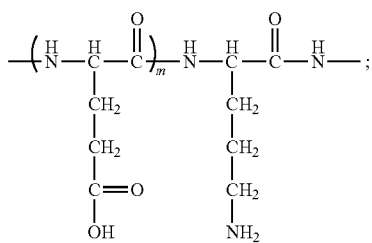

wherein m is 1, 2, 3, or 4.

In other embodiments, the compound can have the formula (II):

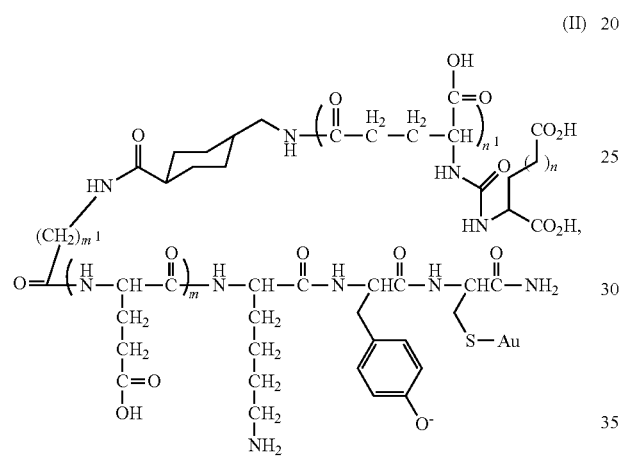

wherein m, n, and $n^1$ are each independently 1, 2, 3, or 4, and wherein $m^1$ is 3-7.

In some embodiments, the plurality of compounds form gold nanoclusters. The gold nanoclusters can include about 10 to about 150 or about 10 to about 40 gold atoms. In some embodiments, the gold nanoclusters can be less than about 10 nm in diameter. In some embodiments, the gold nanoclusters can be less than about 5 nm in diameter.

The gold nanoclusters described herein can be used in methods of detecting and treating cancer. The cancer detected and/or treated can be selected from the group consisting of malignant neoplasms, conventional (clear cell) renal carcinoma, transitional cell carcinoma of the urinary bladder, testicular embryonal carcinoma, colonic adenocarcinoma, neuroendocrine carcinoma, gliobastoma multiforme, malignant melanoma, pancreatic ductal carcinoma, non-small cell lung carcinoma, soft tissue carcinoma, breast carcinoma, and prostatic adenocarcinoma. In some embodiments, the cancer is prostate cancer.

Still other embodiments relate to a method of treating prostate cancer in a subject. The method includes administering systemically (e.g., via intravenous administration) to the subject with cancer a therapeutically effective amount of a composition that includes a gold nanocluster. The gold nanocluster includes a plurality of aggregated compounds having formula (I):

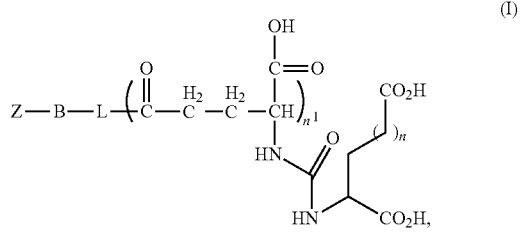

wherein n and $n^1$ are each independently 1, 2, 3, or 4; L is an optionally substituted aliphatic or heteroaliphatic linking group; B comprises at least one negatively charged amino acid; and Z has the formula

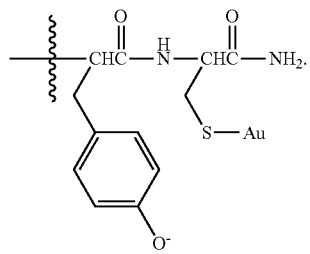

In some embodiments, L can include at least one ring selected from the group consisting of an optionally substituted 4 to 7 membered nonaromatic heterocyclic ring and an optionally substituted C4-C7 cycloalkyl ring.

In some embodiments, B has the following formula:

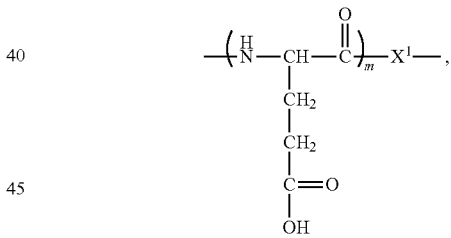

wherein m is 1, 2, 3, or 4, $X^1$ is an amino acid.

In other embodiments, B has the following formula

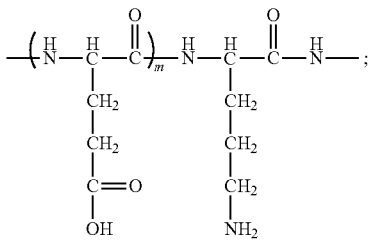

wherein m is 1, 2, 3, or 4.

In other embodiments, the compound can have the formula (II):

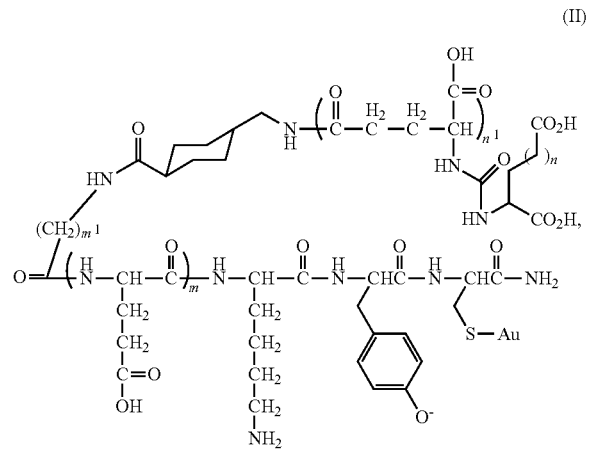

(II)

wherein m, n, and $n^1$ are each independently 1, 2, 3, or 4, and wherein $m^1$ is 3-7.

In some embodiments, the plurality of compounds form gold nanoclusters. The gold nanoclusters can include about 10 to about 150 or about 10 to about 40 gold atoms. In some embodiments, the gold nanoclusters can be less than about 10 nm in diameter. In some embodiments, the gold nanoclusters can be less than about 5 nm in diameter.

After systemic administration of the composition to the subject, the prostate cancer of the subject is irradiated to induce the radiosensitizing effects of the gold nanoparticle targeted thereto. In some embodiments, the prostate cancer can be irradiated using X-ray radiation or gamma radiation. The gold nanocluster selectively targeted to prostate cancer cells of the subject can also be detected to determine the location and/or distribution of the prostate cancer cells in the subject.

In some embodiments, the presence of the gold nanocluster is detected in the subject by at least one positron emission tomography (PET) imaging or computer tomography (CT) imaging.

BRIEF DESCRIPTION OF THE DRAWINGS

FIGS. 2(A-D) illustrates the characterization of CY-PSMA-1-Au$_{25}$NCs. A Distribution of core diameters of CY-PSMA-1-Au$_{25}$NCs. Inset shows a TEM image of Au$_{25}$NCs (scale bar 5 nm). B Distribution of the hydrodynamic diameters of CY-PSMA-1-Au$_{25}$NCs. C Excitation and emission spectra of nanoclusters showing peaks at 490 nm (ex) and 700 nm (em). D MALDI-MS spectra for CY-PSMA-1-Au$_{25}$NCs. A series of intense peaks between 5-12 k m/z fit the formula Au$_{25}$S$_{(18-m)}$P$_m$ (P=CY-PSMA-1) (m=0-18), and the difference between adjacent intense peaks is 1320, which matches the molecular weight of CY-PSMA-1 with one thiol group missing. The inset is an expanded view of peak details in the range 6.2 k-7 k. Space between the minor peaks is 197 m/z and 32 m/z, which corresponds to the loss of Au and S atoms, respectively. Matrix, CHCA, linear model.

FIGS. 3(A-E) illustrates in vitro targeting and radiotherapy of CY-PSMA-1-Au$_{25}$NCs. A. Confocal images of the uptake of CY-PSMA-1-Au$_{25}$NCs by PC3pip and PC3flu cells after 24 h incubation at 30 µg Au/mL. Au$_{25}$NCs show a red fluorescence and DAPI is used for nuclear staining (scale bar 25 µm). B. ICP-MS measurement of Au content in cells, showing significantly higher Au content in PC3pip cells than in PC3flu cells. C. Competition binding curves for parent ZJ24, CY-PSMA-1 ligands, and CY-PSMA-1-Au$_{25}$NCs. D. In vitro ROS generation by a DCFDA assay. Non-fluorescent DCFDA was converted into fluorescent DCF$^-$ by intracellular ROS upon 6 Gy radiation. E Survival curves of PC3pip and PC3flu cells with and without addition of CY-PSMA-1-Au$_{25}$NCs under radiation at doses of 0, 2, 4, and 6 Gy. Data are presented as mean±SD. n=3; two-tailed t-test: *P<0.05.

FIGS. 4(A-D) illustrates tumor uptake and biodistribution of CY-PSMA-1-Au$_{25}$NCs. A. in vivo 3D CT images of the PC3pip (right, blue) and PC3flu (left, green) tumor-bearing mice (indicated by blue and green ovals) before and at 0.5 h, 1 h, 2 h, 4 h, 6 h, and 24 h after intravenous injection of CY-PSMA-1-Au$_{25}$NCs (30 µg Au/g mouse); B. The CT signals at the tumor regions at each time point after CY-PSMA-1-Au$_{25}$NCs injection; C. In vivo 3D CT images of the bladders of mice (indicated by red circles) at each time point; d Biodistribution of CY-PSMA-1-Au$_{25}$NCs in the main organs/urine at 4 h and 24 h post injection, as determined by ICP-MS (data are presented as mean±SD. n=3; two-tailed t-test: *P<0.05).

FIGS. 5(A-C) illustrates clearance of CY-PSMA-1-Au$_{25}$NCs compared with 5 nm AuNPs-PEG$_{2K}$/PSMA-1. A. Au content in liver and urine of mice injected with CY-PSMA-1-Au$_{25}$NCs and 5 nm AuNPs-PEG$_{2K}$/PSMA-1 at 24 h post injection, as determined by ICP-MS (data are presented as mean±SD. n=3; two-tailed t-test: *P<0.05); In vivo 3D CT images of the digestive system of mice injected with B. CY-PSMA-1-Au$_{25}$NCs and C. 5 nm AuNPs-PEG$_{2K}$/PSMA-1 at 24 h post injection, showing more accumulation of 5 nm AuNPs-PEG$_{2K}$/PSMA-1 in the gut than that measured for CY-PSMA-1-Au$_{25}$NCs.

FIGS. 6(A-D) illustrates tumor growth curves and body weight changes of mice after treated with A, B) CY-PSMA-1-Au$_{25}$NCs only and both CY-PSMA-1-Au$_{25}$NCs and 6 Gy radiation, and C, D) PBS only and both PBS and 6 Gy radiation (data are presented as mean±SD. n=3; two-tailed t-test: p≤0.05, p≤0.01).

DETAILED DESCRIPTION

Figure 1A:
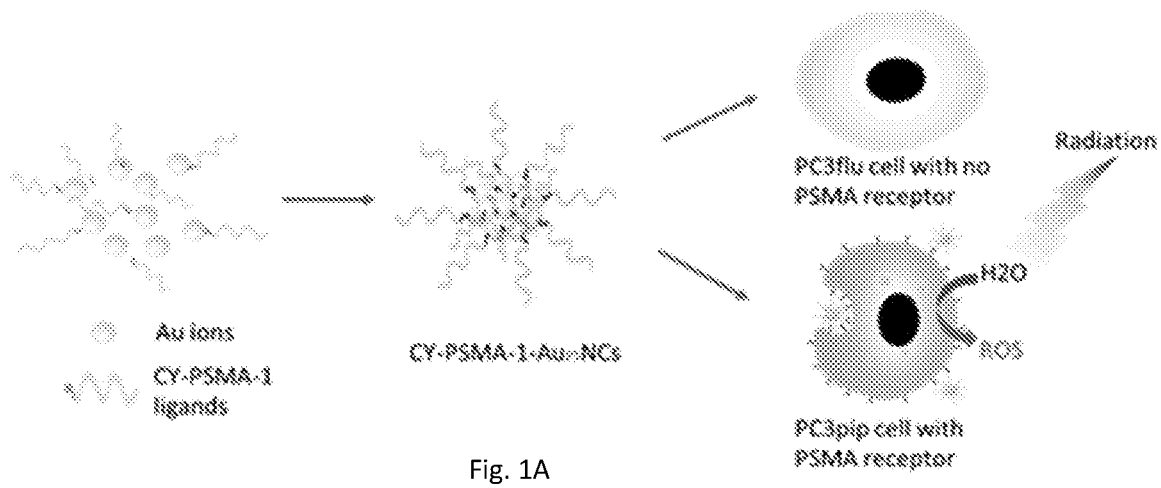
FIGS. 1(A-B) illustrate CY-PSMA-1-Au$_{25}$NCs for targeted radiotherapy of prostate cancer. A Schematic of synthesis of CY-PSMA-1-Au$_{25}$NCs radiosensitizer, with high affinity to the PSMA-expressing PC3pip cells. B Illustration of PC3pip and PC3flu tumor targeting and radiation therapy with CY-PSMA-1-Au$_{25}$NCs. PSMA-expressing PC3pip cells and PSMA-negative PC3flu cells are implanted on the flanks of the same mouse. Intravenous injection of nanoclusters results in higher targeting levels to the PC3pip tumor than to the PC3flu tumor and, thus, improved radiation therapy.

All scientific and technical terms used in this application have meanings commonly used in the art unless otherwise specified. The definitions provided herein are to facilitate understanding of certain terms used frequently herein and are not meant to limit the scope of the application.

The articles "a" and "an" are used herein to refer to one or to more than one (i.e., to at least one) of the grammatical object of the article. By way of example, "an element" means one element or more than one element.

As used herein, the term "sample" can refer to a specimen or culture obtained from any source, as well as clinical, research, biological and environmental samples. Biological samples may be obtained from animals (including humans) and encompass cells, fluids, solids, tissues, and organs, and whole organisms.

As used herein, the term "subject" can refer to any animal including, but not limited to, humans and non-human animals (e.g., rodents, arthropods, insects, fish (e.g., zebrafish)), non-human primates, ovines, bovines, ruminants, lagomorphs, porcines, caprines, equines, or canines felines, aves, etc.).

As used herein, the terms "cancer" or "tumor" refer to any neoplastic growth in a subject, including an initial tumor and any metastases. The cancer can be of the liquid or solid tumor type. Liquid tumors include tumors of hematological origin, including, e.g., myelomas (e.g., multiple myeloma), leukemias (e.g., Waldenstrom's syndrome, chronic lymphocytic leukemia, other leukemias), and lymphomas (e.g., B-cell lymphomas, non-Hodgkin's lymphoma). Solid tumors can originate in organs and include cancers of the lungs, brain, breasts, prostate, ovaries, colon, kidneys and liver.

As used herein, the terms "cancer cell" or "tumor cell" can refer to cells that divide at an abnormal (i.e., increased) rate. Cancer cells include, but are not limited to, carcinomas, such as squamous cell carcinoma, non-small cell carcinoma (e.g., non-small cell lung carcinoma), small cell carcinoma (e.g., small cell lung carcinoma), basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), lymphomas (e.g., follicular lymphoma, mantle cell lymphoma, diffuse large B-cell lymphoma, malignant lymphoma, plasmocytoma, reticulum cell sarcoma, or Hodgkin's disease), and tumors of the nervous system including glioma, glioblastoma multiform, meningoma, medulloblastoma, schwannoma and epidymoma.

"PSMA" refers to Prostate Specific Membrane Antigen, a potential carcinoma marker that can serve as a target for imaging and cytotoxic treatment modalities for cancer.

As used herein, the term "imaging probe" can refer to a biological or chemical moiety that may be used to detect, image, and/or monitor the presence and/or progression of a cell cycle, cell function/physiology, condition, pathological disorder and/or disease.

The term "radiosensitizer" refers to compounds or agents that increase the cytotoxicity of ionizing radiation. For example, heavy-metal nanomaterials with high atomic number (Z) values, such as gold nanomaterials.

As used herein, the terms "treating" or "treatment" of a disease can refer to executing a treatment protocol to eradicate at least one diseased (e.g., cancer cell). Thus, "treating" or "treatment" does not require complete eradication of diseased cells.

As used herein, an "effective amount" can refer to that amount of a therapeutic agent that results in amelioration of symptoms or a prolongation of survival in the subject and relieves, to some extent, one or more symptoms of the disease or returns to normal (either partially or completely) one or more physiological or biochemical parameters associated with or causative of the disease.

As used herein, therapeutic agents can include any agent (e.g., molecule, drug, pharmaceutical composition, etc.) capable of preventing, inhibiting, or arresting the symptoms and/or progression of a disease.

Embodiments described herein relate to PSMA targeted gold compounds and to PSMA targeted gold nanoclusters (AuNCs) that are formed from a plurality of PSMA targeted gold compounds. Additional embodiments relate to compositions including a plurality of PSMA targeted gold compounds or PSMA targeted gold nanoclusters formed thereof, and compositions and methods for treating and detecting cancers (e.g., prostate cancer) in a subject.

The PSMA targeted gold compounds described herein include a gold atom conjugated to a high-affinity PSMA targeting ligand (PSMA-1) that has been modified with cysteine (Cys) and tyrosine (Tyr) residues (CY-PSMA-1 ligand). It was discovered that a PSMA-1 ligand modified to include both the Cys and Tyr residues can conjugate to a gold ion in solution and allow for in-situ synthesis of gold nanoclusters from a plurality of PSMA targeted gold compounds. It was further discovered the Cys and Tyr residues in the CY-PSMA-1 ligand enable reduction and capping of the gold nanoclusters when formed from a plurality of PSMA targeted gold compounds described herein, where the CY-PSMA-1 ligand is stabilized on the AuNC surface via the sulfur-gold ion bond. Further, compositions including a plurality of the PSMA targeted gold compounds and PSMA targeted gold nanoclusters thereof, can be used as high-affinity radiosensitizers in the detection and/or treatment of cancer.

In some embodiments, a CY-PSMA-1 ligand peptide for use in a compound and compositions described herein can have the amino acid sequence Glu-CO-Glu'-Amc-Ahx-Glu-Glu-Glu-Lys-Tyr-Cys-NH2. A CY-PSMA-1 peptide can be synthesized using a solution/solid system. For example, a CY-PSMA-1 ligand can be synthesized manually using standard Fmoc solid-phase peptide synthesis (SPPS) chemistry. The CY-PSMA-1 ligands can be mixed with $Au^{3+}$ ions, where the gold ions reduce and complex with the peptide ligand.

In some embodiments, a PSMA targeted gold compound can have formula (I):

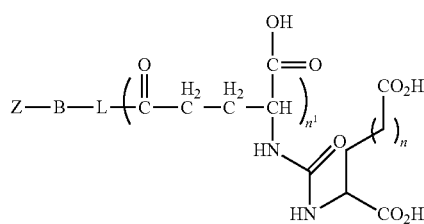

wherein:

n and $n^1$ are each independently 1, 2, 3, or 4;

L is an optionally substituted aliphatic or heteroaliphatic linking group;

B comprises at least one negatively charged amino acid; and

Z has the formula

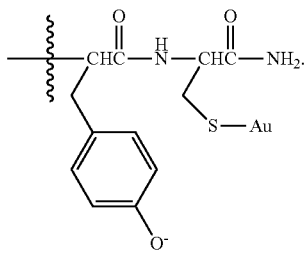

In some embodiments, B can include at least one, two, three, four, or more negatively charged amino acids, i.e., amino acids with a negative charged side chain, such as glutamic acid, aspartic acid, and/or tyrosine. In particular embodiments, B has the following formula:

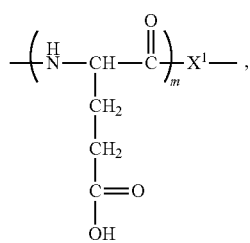

wherein m is 1, 2, 3, or 4, and $X^1$ is an amino acid.

In other embodiments, B has the following formula:

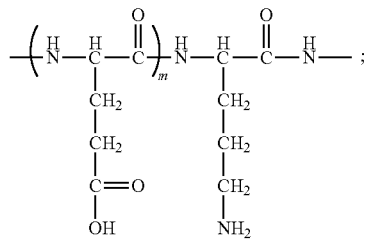

wherein m is 1, 2, 3, or 4.

In some embodiments, L can include at least one ring selected from the group consisting of an optionally substituted 4 to 7 membered nonaromatic heterocyclic ring and an optionally substituted C4-C7 cycloalkyl ring.

Suitable optional substituents for a substitutable atom in alkyl, cycloalkyl, aliphatic, cycloaliphatic, heterocyclic, benzylic, aryl, or heteroaryl groups described herein are those substituents that do not substantially interfere with the activity of the disclosed compounds. A "substitutable atom" is an atom that has one or more valences or charges available to form one or more corresponding covalent or ionic bonds with a substituent. For example, a carbon atom with one valence available (e.g., —C(—H)=) can form a single bond to an alkyl group (e.g., —C(-alkyl)=), a carbon atom with two valences available (e.g., —C($H_2$)—) can form one or two single bonds to one or two substituents (e.g., —C(alkyl)(Br))—, —C(alkyl)(H)—) or a double bond to one substituent (e.g., —C=O)—), and the like. Substitutions contemplated herein include only those substitutions that form stable compounds.

For example, suitable optional substituents for substitutable carbon atoms include —F, —Cl, —Br, —I, —CN, —$NO_2$, —$OR^a$, —$C(O)R^a$, —$OC(O)R^a$, —$C(O)OR^a$, —$SR^a$, —$C(S)R^a$, —$OC(S)R^a$, —$C(S)OR^a$, —$C(O)SR^a$, —$C(S)SR^a$, —$S(O)R^a$, —$SO_2R^a$, —$SO_3R^a$, —$POR^aR^b$, $PO_2R^aR^b$, —$PO_3R^aR^b$, —$PO_4R^aR^b$, —$P(S)R^aR^b$, —$P(S)$ $OR^aR^b$, —$P(S)O_2R^aR^b$, —$P(S)O_3R^aR^b$, —$N(R^aR^b)$, —$C(O)N(R^aR^b)$, —$C(O)NR^aNR^bSO_2R^c$, —$C(O)$ $NR^aSO_2R^c$, —$C(O)NR^aCN$, —$SO_2N(R^aR^b)$, —$SO_2N$ $(R^aR^b)$, —$NR^cC(O)R^a$, —$NR^cC(O)OR^a$, —$NR^cC(O)N$ $(R^aR^b)$, —$C(NR^c)$—$N(R^aR^b)$, —$NR^d$—$C(NR^c)$—$N(R^aR^b)$, —$NR^aN(R^aR^b)$, —CRC=$CR^aR^b$, —C=$CR^a$, =O, =S, =$CR^aR^b$, =$NR^a$, =$NOR^a$, =$NNR^a$, optionally substituted alkyl, optionally substituted cycloalkyl, optionally substituted aliphatic, optionally substituted cycloaliphatic, optionally substituted heterocyclic, optionally substituted benzyl, optionally substituted aryl, and optionally substituted heteroaryl, wherein $R^a$—$R^d$ are each independently —H or an optionally substituted aliphatic, optionally substituted cycloaliphatic, optionally substituted heterocyclic, optionally substituted benzyl, optionally substituted aryl, or optionally substituted heteroaryl, or, —$N(R^aR^b)$, taken together, is an optionally substituted heterocyclic group. Also contemplated are isomers of these groups.

In other embodiments, the compound can have the formula (II):

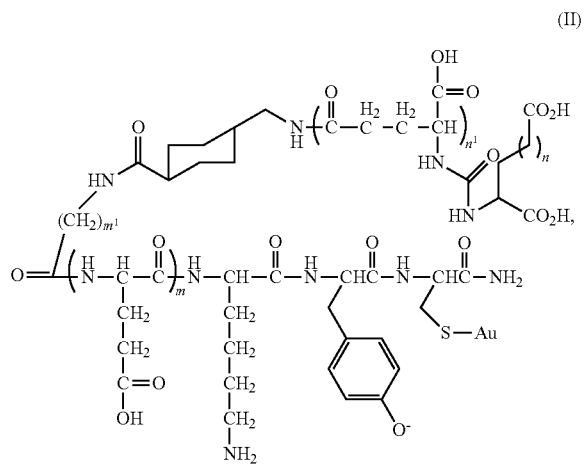

(II)

wherein m, n, and $n^1$ are each independently 1, 2, 3, or 4, and wherein $m^1$ is 3-7.

In some embodiments, a plurality of compounds that include formula (I) can aggregate form a PSMA targeted gold nanocluster (AuNC). In an exemplary embodiment, PSMA targeted AuNC synthesis can occur by CY-PSMA-1 ligand reduction and stabilization where the cysteine residue captures $Au^{3+}$ ions in solution with the thiol group and a pH increase from the addition of NaOH in the solution turns the phenolic group of the tyrosine residue into a phenoxide ion, which can reduce $Au^{3+}$ ions. The resultant Au atoms can then aggregate to form gold nanoclusters where the gold nanoclusters are stabilized via thiol groups of the CY-PSMA-1 cysteine residues.

The PSMA targeted gold nanoclusters can exhibit discrete optical and electronic states characterized by, for example, strong quantum effects and fluorescence, which allows the gold nanoclusters to behave as molecular, rather than metallic substances. This molecular optical and electronic behavior sharply distinguishes the PSMA-targeted gold nanoclusters from gold nanoparticles whose optical characteristics can be driven by plasmon resonance.

In some embodiments, an PSMA targeted AuNC formed from a plurality of compounds that include formula (I) as described herein can each include about 10 to about 150 gold atoms. In some embodiments, the gold nanoclusters include about 10 to about 40 gold atoms or about 10 to about 12 gold atoms. In particular embodiments, a gold nanocluster can include 15, 18, 22, 25, 39 or 144 gold atoms. In an exemplary embodiment, a PSMA targeted AuNC formed from a plurality of compounds that include formula (I) as described herein can include 25 gold atoms. For example, PSMA targeted AuNCs for use in a composition describe herein including 25 gold nanoparticles can have the formula $Au_{25}S_{(18-m)}(P_m)$, where P=CY-PSMA-1 and m=1-18.

In some embodiments, PSMA targeted AuNCs for use in a composition describe herein can have an average diameter less than about 10 nm. In order to reduce nanoparticle-induced toxicity compared to larger particles, PSMA targeted AuNCs formed as described herein can be small enough (e.g., less than about 5.5 nm) to be excreted from urine. In some embodiments, PSMA targeted AuNCs for use in a composition describe herein can have an average diameter less than about 5 nm. In particular embodiments, a PSMA targeted AuNC can have an average diameter of about 1.5 nm. An exemplary PSMA targeted AuNC for use in a composition describe herein can have an average diameter of 1.5±0.5 nm and a hydrodynamic diameter of 3.0 nm.

It was found that the PSMA targeted compounds and the nanoclusters (AuNCs) formed from a plurality of compounds described herein upon systemic administration (e.g., intravenous injection) preferentially accumulate at PSMA-expressing tumor tissue via active targeting. The PSMA targeted gold compounds and PSMA targeted gold nanoclusters thereof can target and transiently interact with, bind to, and/or couple with a PSMA expressing cancer cell, such as a prostate cancer cell, and once interacting with, bound to, or coupled to the targeted cancer cell or tissue advantageously facilitate delivery of gold atoms within cell by, for example, receptor mediated endocytosis. It was further found that AuNCs accumulation in vivo via active PSMA targeting can enhance the efficacy of focalized radiation treatment in a subject.

Therefore, additional embodiments, relate to the use of compositions including a plurality of PSMA targeted compounds that include formula (I) or PSMA targeted gold nanoclusters formed thereof as described herein for the detection and/or treatment of cancer in a subject.

When compositions including the PSMA targeted compounds or PSMA targeted nanoclusters thereof described herein are used as molecular imaging probes, the compounds or nanoclusters can precisely localize and clearly demarcate the cancer cells in tissue sections and tumor "edge" samples, suggesting that the compounds and nanocluster formed thereof can be used as diagnostic tools for molecular imaging of metastatic, dispersive, migrating, or invading cancers or the tumor margin.

The compositions described herein can therefore be used in a method of detecting cancer cells and/or cancer cell metastasis, migration, dispersal, and/or invasion as well as in a method of treating cancer in a subject in need thereof. The methods can include administering to a subject a diagnostically and/or therapeutically effective amount of a composition including a PSMA targeted compound that includes formula (I) or PSMA targeted gold nanoclusters formed thereof described herein and detecting the compounds or gold nanoclusters selectively targeted to PSMA expressing cancer cells and/or cancer tissue.

Pathological studies indicate that PSMA is expressed by virtually all prostate cancers, and its expression is further increased in poorly differentiated, metastatic, and hormone-refractory carcinomas. Higher PSMA expression is also found in cancer cells from castration-resistant prostate cancer patients. Increased PSMA expression is reported to correlate with the risk of early prostate cancer recurrence after radical prostatectomy. In addition to being overexpressed in prostate cancer (PCa), PSMA is also expressed in the neovasculature of neoplasms including but not limited to conventional (clear cell) renal carcinoma, transitional cell carcinoma of the urinary bladder, testicular embryonal carcinoma, colonic adenocarcinoma, neuroendocrine carcinoma, gliobastoma multiforme, malignant melanoma, pancreatic ductal carcinoma, non-small cell lung carcinoma, soft tissue carcinoma, breast carcinoma, and prostatic adenocarcinoma.

In some embodiments, the PSMA targeted compounds or PSMA targeted gold nanoclusters described herein, can be used as high-affinity radiosensitizers to detect and/or treat the PSMA-expressing tumors, cancer cells, and/or cancer neovasculature in a subject.

For example, the compositions including PSMA targeted compounds or PSMA targeted gold nanoclusters described herein can be administered systemically to a subject and selectively target PSMA-expressing cancer cells. In some embodiments, the compounds or gold nanoclusters of a composition described herein after systemic administration can define PSMA-expressing cancer cell location, distribution, metastases, dispersions, migrations, and/or invasion as well as tumor cell margins in the subject. In other embodiments, the compounds or gold nanoclusters after systemic administration of a composition described herein can be used to inhibit and/or reduce cancer cell survival, proliferation, and migration.

The PSMA cancer that is detected and/or treated using a composition described herein can include but is not limited to glioma, lung cancer, melanoma, breast cancer, and prostate cancer. In some embodiments, the PSMA expressing cancer that is detected and/or treated is prostate cancer. In other embodiments, the cancer that is detected and/or treated can include malignant neoplasms, such a conventional (clear cell) renal carcinoma, transitional cell carcinoma of the urinary bladder, testicular embryonal carcinoma, colonic adenocarcinoma, neuroendocrine carcinoma, gliobastoma multiforme, malignant melanoma, pancreatic ductal carcinoma, non-small cell lung carcinoma, soft tissue carcinoma, breast carcinoma, and prostatic adenocarcinoma.

In some embodiments, compositions including a plurality of PSMA targeted compounds or PSMA targeted gold nanoclusters described herein may be used in conjunction with non-invasive imaging (e.g., neuroimaging) techniques for in vivo imaging of PSMA targeted gold compounds or nanoclusters thereof. The term "in vivo imaging" refers to any method, which permits the detection of a PSMA targeted compound or PSMA targeted nanocluster thereof.

The PSMA targeted compounds and PSMA targeted gold nanoclusters formed thereof can be detected in vivo by detecting, recognizing, or imaging the agent by one or more imaging modalities capable of imaging gold particles in vivo. In some embodiments, gamma imaging, such as positron emission tomography (PET) or single-photon emission computed tomography (SPECT) can be employed for in vivo imaging. In some embodiments, an X-ray contrast based imaging modality such as but not limited to computer tomography (CT), radiography, and/or fluoroscopy can be employed.

In certain embodiments, the PSMA targeted compounds and PSMA targeted gold nanoclusters formed thereof can be detected in vivo by detecting, recognizing, or imaging the agents by computer tomography (CT) imaging. In some embodiments, a multimodality system, such as a PET/CT Multimodality System, can be used for detecting, recognizing, or imaging the compounds and gold nanoclusters described herein in vivo.

In an exemplary embodiment, a subject can be administered PSMA targeted gold nanoclusters at a dose of 5 mg Au/kg. The subject can be scanned using a PET/CT system before administration and at 0.5, 1 h, 2 h, 6 h and 24 hours after intravenous injection. CT scanning can be performed at tube voltage of 70 k V, current of 300 u A, and gantry rotation time of 140 ms. Three-dimensional CT images acquired can be reconstructed and Hounsfield unit quantified at tumor areas. In certain embodiments, the CT signal generated is a direct reflection of the Au atom concentration at a particular site in vivo.

Diagnostic compositions including a plurality of PSMA targeted compounds or PSMA targeted nanoclusters thereof described herein can be administered to the subject by, for example, systemic, topical, and/or parenteral methods of administration. These methods include, e.g., injection, infusion, deposition, implantation, or topical administration, or any other method of administration where access to the cells and/or tissue by the agents of a compositions described herein is desired. In one example, administration of a composition described herein can be by intravenous injection of the composition in the subject. Single or multiple administrations of the compositions can be given. "Administered", as used herein, means provision or delivery of compositions in an amount(s) and for a period of time(s) effective to label cancer cells in the subject.

Compositions including a plurality of PSMA targeted compounds or nanoclusters thereof described herein can be administered to a subject in a diagnostically effective amount (e.g., a detectable quantity) of a pharmaceutical composition or a pharmaceutically acceptable water-soluble salt thereof, to a subject. A "detectable quantity" means that the amount of the detectable compound that is administered is sufficient to enable detection of binding and/or uptake of the compound or gold nanoclusters to the cancer cells. An "imaging effective quantity" means that the amount of the detectable compound or nanoclusters that is administered is sufficient to enable imaging of binding and/or uptake of the compound or nanoclusters to the cancer cells.

Formulation of the compositions to be administered will vary according to the route of administration selected (e.g., solution, emulsion, capsule, and the like). Suitable pharmaceutically acceptable carriers may contain inert ingredients which do not unduly inhibit the biological activity of the compounds or gold nanoclusters. The pharmaceutically acceptable carriers should be biocompatible, e.g., non-toxic, and devoid of other undesired reactions upon the administration to a subject. Standard pharmaceutical formulation techniques can be employed, such as those described in Remington's Pharmaceutical Sciences, ibid. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like.

The preparation of a pharmacological composition that contains active ingredients dissolved or dispersed therein is well understood in the art. Typically, such compositions are prepared as injectables either as liquid solutions or suspensions, however, solid forms suitable for solution, or suspensions, in liquid prior to use can also be prepared. Formulation will vary according to the route of administration selected (e.g., solution, emulsion, capsule).

The compositions administered to a subject can be used in a method to detect and/or determine the presence, location, and/or distribution of cancer cells expressing PSMA in an organ or body area of a patient, e.g., at least one region of interest (ROI) of the subject. The ROI can include a particular area or portion of the subject and, in some instances, two or more areas or portions throughout the entire subject. The ROI can include regions to be imaged for both diagnostic and therapeutic purposes. The ROI is typically internal; however, it will be appreciated that the ROI may additionally, or alternatively, be external.

The presence, location, and/or distribution of a plurality of PSMA targeted compounds or PSMA targeted gold nanoparticles in the animal's tissue, e.g., prostate tumor tissue, can be visualized (e.g., with an in vivo imaging modality described above). "Distribution" as used herein is the spatial property of being scattered about over an area or volume. In this case, "the distribution of cancer cells" is the spatial property of cancer cells being scattered about over an area or volume included in the animal's tissue, e.g., tumor tissue.

The distribution of the PSMA targeted compound or PSMA targeted nanoclusters may then be correlated with the presence or absence of cancer cells in the tissue. A distribution may be dispositive for the presence or absence of a cancer cells or may be combined with other factors and symptoms by one skilled in the art to positively detect the presence or absence of migrating or dispersing cancer cells, cancer metastases or define a tumor margin in the subject. It will be appreciated that the imaging modality may be used to generate a baseline image prior to administration of the compositions. In this case, the baseline and post-administration images can be compared to ascertain the presence, absence, and/or extent of a particular disease or condition.

In one aspect, compositions described herein may be administered to a subject to assess the distribution of cancer cells in a subject and correlate the distribution to a specific location. Compositions described herein that include PSMA targeted compounds and PSMA targeted gold nanoclusters selectively target PSMA expressing cancer cells can be used in intra-operative imaging (IOI) techniques to guide surgical resection and eliminate the "educated guess" of the location of the tumor margin by the surgeon. It is anticipated that PSMA targeted compounds and PSMA targeted gold nanoclusters that function as diagnostic molecular imaging agents have the potential to increase patient survival rates.

In some embodiments, to identify and facilitate removal of cancers cells, microscopic intra-operative imaging (IOI) techniques can be combined with systemically administered or locally administered compositions described herein. The PSMA targeted gold nanoclusters upon administration to the subject can target and detect and/or determine the presence, location, and/or distribution of cancer cells, i.e., cancer cells expressing PSMA, in an organ or body area of a patient. In one example, the compositions can be combined with IOI to identify malignant cells that have infiltrated and/or are beginning to infiltrate at a tumor margin. The method can be performed in real-time during surgery. An imaging modality described above, such a CT imaging modality, can then be used to detect and subsequently gather image data. The resultant image data may be used to determine, at least in part, a surgical and/or radiological treatment. Alternatively, this image data may be used to control, at least in part, an automated surgical device (e.g., laser, scalpel, micromachine) or to aid in manual guidance of surgery. Further, the image data may be used to plan and/or control the delivery of a therapeutic agent (e.g., by a micro-electronic machine or micro-machine).

Another embodiment described herein relates to a method of monitoring the efficacy of a cancer therapeutic or cancer therapy administered to a subject. The methods and compositions described herein can be used to monitor and/or compare the invasion, migration, dispersal, and metastases of a cancer in a subject prior to administration of a cancer therapeutic or cancer therapy, during administration, or post therapeutic regimen.

A "cancer therapeutic" or "cancer therapy", as used herein, can include any agent or treatment regimen that is capable of negatively affecting cancer in an animal, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of an animal with cancer. Cancer therapeutics can include one or more therapies such as, but not limited to, chemotherapies, radiation therapies, hormonal therapies, and/or biological therapies/immunotherapies. A reduction, for example, in cancer volume, growth, migration, and/or dispersal in a subject may be indicative of the efficacy of a given therapy. This can provide a direct clinical efficacy endpoint measure of a cancer therapeutic. Therefore, in another aspect, a method of monitoring the efficacy of a cancer therapeutic is provided. More specifically, embodiments of the application provide for a method of monitoring the efficacy of a cancer therapy The cancer therapeutics can include therapeutic agents effective for the treatment of PSMA positive cancers. The cancer therapeutic agents can be in the form of biologically active ligands, small molecules, peptides, polypeptides, proteins, DNA fragments, DNA plasmids, interfering RNA molecules, such as siRNAs, oligonucleotides, and DNA encoding for shRNA.

The method of monitoring the efficacy of a cancer therapeutic can include the steps of administering in vivo to the animal a composition as described herein, then visualizing a distribution of the nanoparticle agents in the animal (e.g., with an in vivo imaging modality as described herein), and then correlating the distribution of the molecular probe with the efficacy of the cancer therapeutic. It is contemplated that the administering step can occur before, during, and after the course of a therapeutic regimen in order to determine the efficacy of a chosen therapeutic regimen. One way to assess the efficacy of the cancer therapeutic is to compare the distribution of a molecular probe pre and post cancer therapy.

In some embodiments, the PSMA targeted compounds or PSMA targeted gold nanoclusters are detected in the subject to detect and/or provide the location and/or distribution of the cancer cells in the subject. The location and/or distribution of the cancer cells in the subject can then be compared to a control to determine the efficacy of the cancer therapeutic and/or cancer therapy. The control can be the location and/or distribution of the cancer cells in the subject prior to the administration of the cancer therapeutic and/or cancer therapy. The location and/or distribution of the cancer cells in the subject prior to the administration of the cancer therapeutic and/or cancer therapy can be determined by administering the composition to the subject and detecting the PSMA targeted compounds or PSMA targeted gold nanoclusters selectively targeted to PSMA expressing cancer cells in the subject prior to administration of the cancer therapeutic and/or cancer therapy.

In certain embodiments, the methods and compositions described herein can be used to measure the efficacy of a therapeutic administered to a subject for treating a metastatic, invasive, or dispersed cancer. In these embodiments, the compositions can be administered to the subject prior to, during, or post administration of the therapeutic regimen and the distribution of cancer cells can be imaged to determine the efficacy of the therapeutic regimen. In one example, the therapeutic regimen can include a surgical resection of the metastatic cancer and the nanoparticle agents can be used to define the distribution of the metastatic cancer pre-operative and post-operative to determine the efficacy of the surgical resection. Optionally, the methods and compositions can be used in an intra-operative surgical procedure as described above, such as a surgical tumor resection, to more readily define and/or image the cancer cell mass or volume during the surgery.

As described in the Example, PSMA targeted compounds and PSMA targeted gold nanoclusters described herein can act as a radiosensitizer to enhance the ablation of cancer (e.g., prostate cancer) using a low radiation dose. In certain embodiments, the compounds and gold nanoclusters enable CT-image guided radiation therapy to enhance radiation accuracy and to avoid collateral damage to normal tissues. Radiation can be administered to targeted cancer cells or tissue using external beam radiotherapy. Radiation administered can include, but is not limited to gamma and X-ray radiation.

In an exemplary embodiment, a radiation dose of 6gy of X-ray radiation can be administered to detected cancer cells or cancer tissue following the injection of a composition including a plurality of the PSMA targeted gold nanoclusters at a dose of 30 μg Au/g. In certain embodiments, the radiation dose is administered between about 2 to about 8 hours after injection of the PSMA targeted gold nanocluster composition. In a particular embodiment, the radiation dose can be administered about 4 hours after injection of the PSMA targeted gold nanocluster compositions to the subject.

Therapeutic compositions described herein can be administered to a subject by any conventional method of drug administration, for example by parenteral administration. Parenteral administration can include, for example, intramuscular, intravenous, intraventricular, intraarterial, intrathecal, subcutaneous, or intraperitoneal administration. The disclosed compositions can also be administered orally (e.g., in capsules, suspensions, tablets or dietary), nasally (e.g., solution, suspension), transdermally, intradermally, topically (e.g., cream, ointment), inhalation (e.g., intrabronchial, intranasal, oral inhalation or intranasal drops) transmucosally or rectally. Delivery can also be by injection into the brain or body cavity of a patient or by use of a timed release or sustained release matrix delivery systems, or by onsite delivery using micelles, gels and liposomes. Nebulizing devices, powder inhalers, and aerosolized solutions may also be used to administer such preparations to the respiratory tract. Delivery can be in vivo, or ex vivo. Administration can be local or systemic as indicated. More than one route can be used concurrently, if desired. The preferred mode of administration can vary depending upon the particular disclosed composition chosen. In specific embodiments, parenteral, or systemic administration are preferred modes of administration for treatment.

The compositions described herein can be administered alone as a monotherapy, or in conjunction with or in combination with one or more additional therapeutic agents. For example, the compositions described herein can be administered to the subject prior to, during, or post administration of an additional therapeutic agent and the distribution of metastatic cells can be targeted with the therapeutic agent. The PSMA targeted compounds and PSMA targeted gold nanoclusters can be administered to an animal subject as part of a pharmaceutical composition comprising the compounds or gold nanoclusters and a pharmaceutically acceptable carrier or excipient and, optionally, one or more additional therapeutic agents. The compounds and gold nanoclusters described herein and one or more additional therapeutic agent(s) can be components of separate pharmaceutical compositions, which can be mixed together prior to administration or administered separately. The PSMA targeted compounds and PSMA targeted gold nanoclusters described herein can, for example, be administered in a pharmaceutical composition containing the additional therapeutic agent, and thereby, administered contemporaneously with the agent. Alternatively, the compositions including PSMA targeted compounds and PSMA targeted gold nanoclusters described herein can be administered contemporaneously, without mixing (e.g., by delivery of the composition on the intravenous line by which the therapeutic agent is also administered, or vice versa). In another embodiment, the compositions described herein can be administered separately (e.g., not admixed), but within a short time frame (e.g., within 24 hours) of administration of the therapeutic agent.

The methods described herein contemplate single as well as multiple administrations, given either simultaneously or over an extended period of time. The compounds and gold nanoclusters described herein (or composition containing the agents) can be administered at regular intervals, depending on the nature and extent of the cancer's effects, and on an ongoing basis. Administration at a "regular interval," as used herein, indicates that the therapeutically effective amount is administered periodically (as distinguished from a one-time dose). In one embodiment, a composition including a plurality of compounds or gold nanoclusters and/or an additional therapeutic agent is administered periodically, e.g., at a regular interval (e.g., bimonthly, monthly, biweekly, weekly, twice weekly, daily, twice a day or three times or more often a day).

The administration interval for a single individual can be fixed, or can be varied over time, depending on the needs of the individual. For example, in times of physical illness or stress, or if disease symptoms worsen, the interval between doses can be decreased. In some embodiments, the composition can be administered between, for example, once a day or once a week.

In some embodiments, the administration of the disclosed compositions and/or the additional therapeutic agent can take place at least once on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least once on week 1, 2, 3, 4, 5, 6, 7, 8, 9, 10, 11, 12, 13, 14, 15, 16, 17, 18, 19 or 20, or any combination thereof, using single or divided doses of every 60, 48, 36, 24, 12, 8, 6, 4, or 2 hours, or any combination thereof. Administration can take place at any time of day, for example, in the morning, the afternoon or evening. For instance, the administration can take place in the morning, e.g., between 6:00 a.m. and 12:00 noon; in the afternoon, e.g., after noon and before 6:00 p.m.; or in the evening, e.g., between 6:01 p.m. and midnight.

The disclosed compositions described herein and/or additional therapeutic agent can be administered in a dosage of, for example, 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day. Dosage forms (composition) suitable for internal administration generally contain from about 0.1 milligram to about 500 milligrams of active ingredient per unit. In these pharmaceutical compositions, the active ingredient will ordinarily be present in an amount of about 0.5-95% by weight based on the total weight of the composition.

The amount of disclosed compositions described herein and/or additional therapeutic agent administered to the subject can depend on the characteristics of the subject, such as general health, age, sex, body weight and tolerance to drugs as well as the degree, severity and type of rejection. The skilled artisan will be able to determine appropriate dosages depending on these and other factors using standard clinical techniques.

In addition, in vitro or in vivo assays can be employed to identify desired dosage ranges. The dose to be employed can also depend on the route of administration, the seriousness of the disease, and the subject's circumstances. Effective doses may be extrapolated from dose-response curves derived from in vitro or animal model test systems. The amount of the PSMA targeted compounds and PSMA targeted gold nanoclusters described herein can also depend on the disease state or condition being treated along with the clinical factors and the route of administration of the PSMA targeted compounds or PSMA targeted gold nanoclusters.

For treating humans or animals, the amount of disclosed compositions and/or additional therapeutic agent administered (in milligrams of compound per kilograms of subject body weight) is generally from about 0.1 mg/kg to about 100 mg/kg, typically from about 1 mg/kg to about 50 mg/kg, or more typically from about 1 mg/kg to about 25 mg/kg. In a preferred embodiment, the effective amount of PSMA targeted compound or PSMA targeted gold nanoclusters described herein is about 0.1-50 mg/kg. In another preferred embodiment, the effective amount of PSMA targeted compounds or PSMA targeted gold nanoclusters is about 10-40 mg/kg. The effective amount for a subject can be varied (e.g., increased or decreased) over time, depending on the needs of the subject. In an exemplary embodiment, the PSMA targeted gold nanoclusters are administered via intravenous injection at a dose of 30 mg Au/kg body weight of a subject in need thereof.

The following examples are for the purpose of illustration only and are not intended to limit the scope of the claims, which are appended hereto.

EXAMPLE

In this example, we have developed ultrasmall $Au_{25}$ nanoclusters (NCs) for selective prostate cancer targeting, radiotherapy enhancement, and rapid clearance from the body. Targeted-$Au_{25}$ NCs are rapidly and selectively taken up by prostate cancer in vitro and in vivo and also have fast renal clearance. When combined with x-ray irradiation of the targeted cancer tissues, radiotherapy was significantly enhanced. The selective targeting and rapid clearance of the nanoclusters allow for significant reductions in radiation dose, decreasing exposure to healthy tissue, and making them highly attractive for clinical practice.

Prostate cancer is the most diagnosed cancer among men in the United States. For treatment of prostate cancer, radical prostatectomy still remains the most direct and effective approach. However, when the cancer has extended beyond the prostate, surgery may be unable to remove all the malignant nodules, resulting in a high recurrence rate of the cancer. In this case, radiation therapy is often necessary to reduce surgery-related morbidities. More than half of the patients receive radiation in the form of electrons, protons or photons (gamma- or X-rays) during their battle against cancers. However, in the practice of radiation treatment, normal tissue is also exposed and potential radiotoxicity is, thus, unavoidable. Advances of radiotherapy, such as megavolt (6-25 MV) X-rays, tomotherapy, and intensity-modulated radiation therapy (IMRT), allow one to minimize damage to normal tissue and to better focus the radiation to the tumor. However, radiotherapy alone is less likely to succeed when the tumor cells are radioresistant (e.g. hypoxic), under-irradiated, or outside the targeted region.

Radiosensitizers increase the effects of radiation dose in the cancer region on the cellular level and enhance the outcome of radiation therapy, even for radioresistant resistant cells, while simultaneously lowering off-target radiation doses. Materials with a high atomic numbers (Z) (e.g., iodine, gadolinium, and gold), exhibit high x-ray absorption coefficients. Upon x-ray radiation, such radiosensitizers can generate secondary radiation in the form of scattered photons, electrons, electron-positron pairs, or fluorescence, which can compromise and kill the cancer cells. The radiation enhancement is especially outstanding for gold (Z=79). Gold has a much higher absorbance of radiation compared to normal tissue with up to a 100-fold enhancement in the keV energy range, and gold is, among the above-mentioned high-Z elements, the most biocompatible element.

Figure 1B:
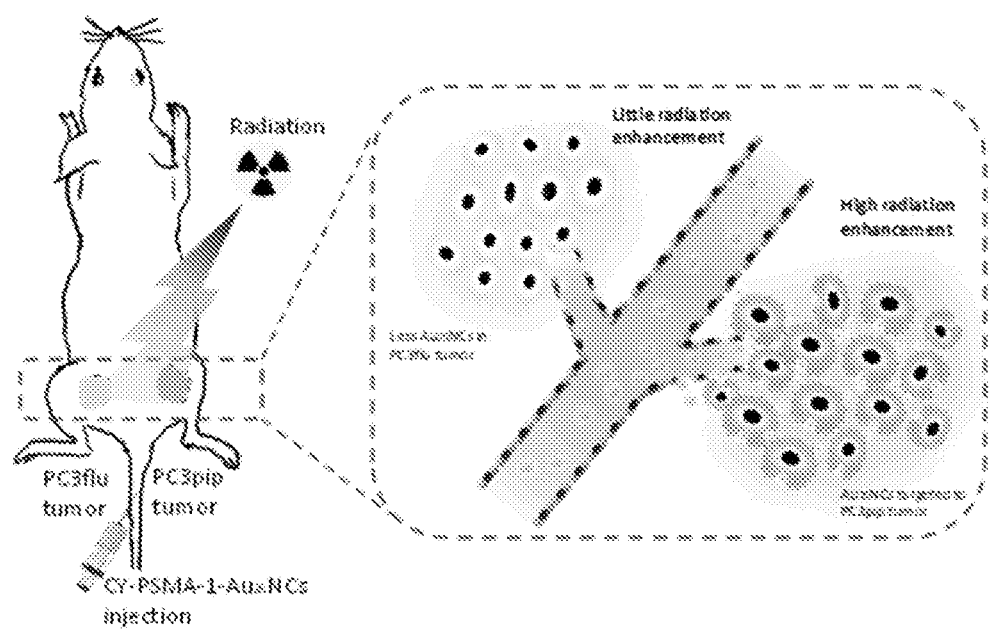

Here, we present a highly specific radiosensitizing probe for prostate cancer therapy based on the prostate specific membrane antigen, PSMA. PSMA is a type II membrane protein, which is highly expressed in most prostate cancers. It is not secreted and is membrane bound, making it an attractive extracellular target for therapeutic probes for prostate cancer. We have developed a high-affinity PSMA targeting ligand (PSMA-1) and demonstrated its use in prostate cancer imaging and photodynamic therapy. Here the PSMA-1 ligand is further modified for in-situ synthesis of PSMA-1-targeted $Au_{25}$ nanoclusters (CY-PSMA-1-$Au_{25}$NCs), providing a high-affinity and highly effective radiosensitizer for prostate cancer that is also small enough to be excreted by the kidneys within hours. The resulting CY-PSMA-1-$Au_{25}$NCs effectively enhanced the targeted radiotherapy in vivo and fast renal elimination may simultaneously reduce the sensitizer-induced off-target and elemental toxicity (FIG. 1).

To address the challenges for developing a highly selective gold-based radiation sensitizer, we have utilized the highly-selective PSMA ligand for prostate cancer and combined it with AuNCs of 1.5 nm in diameter, which is well below the threshold for renal clearance (~5.5 nm) and therefore reduces unintended and nonspecific organ uptake by the liver and spleen as well as any potential gold cluster induced organ toxicity.

Methods

Synthesis of CY-PSMA-1 Ligand

CY-PSMA-1 peptide with the sequence Glu-CO-Glu'-Amc-Ahx-Glu-Glu-Glu-Lys-Tyr-Cys-$NH_2$ was synthesized manually using a standard Fmoc chemistry. CY-PSMA-1 synthesis was initiated by reacting 3.3 equivalents of Fmoc-Cys(Trt)-OH with 0.2 mmol C-terminated Fmoc-rink amide MBHA resin in DMF. 3.3 and 5 equiv of HCTU and diisopropylethylamine (DIPEA) were added as coupling agents. Fmoc was removed using 20% piperidine in DMF before addition of the next amino acid. After the sequence Glu'-Amc-Ahx-Glu-Glu-Glu-Lys(Boc)-Tyr-Cys(Trt) was conjugated to the resin, the Fmoc of Glu' was removed with 20% piperidine and the resin was swollen in chloroform with 2.5 equiv of DIPEA. Then, the Glu-COOH pre-conjugation was prepared by mixing 3 equiv of H-Glu(OtBu)-OtBu with 2.5 equiv of DIPEA in chloroform, which was then then added slowly to 0.25 equiv of triphosgene in chloroform and reacted for 15 min. The reacting mixture was then added to the resin and reacted for another 45 min. Finally, after the mixture reacted, the resin was washed with DMF and methanol respectively, and dried. The peptide was cleaved from the resin with a cleavage cocktail of TFA/$H_2O$/triisopropylsilane (95%/2.5%/2.5%) and precipitated with cold diethyl ether before purification by HPLC. The synthesized PSMA-1 peptides were characterized by electrospray ionization mass spectrometry (ESI-MS, LCQ advantage, Thermo Finnigan).

Synthesis of CY-PSMA-1-$Au_{25}$NCs

CY-PSMA-1-$Au_{25}$NCs were synthesized using a one-step method. The CY-PSMA-1 peptides were dissolved in $H_2O$ (1.0 mM) and the pH of the peptide solution was adjusted to around 7. Then, 160 ul of 25 mM HAuCl$_4$ aqueous solution was added dropwise to 4 mL CY-PSMA-1 solution with vigorous stirring. After a few minutes, 0.5 M NaOH solution was added quickly to bring the pH up to around 12. The mixture was stored in the dark and allowed to react for 15 h. Next, the reaction mixture was purified by dialysis against 25 mM HEPES buffer (pH 7.8) for 2 h, and then against 12.5 mM HEPES buffer (pH 7.8) for 24 h to remove excess ions and CY-PSMA-1 ligand. The purified product was then lyophilized and stored in −20° C. for future use. PSMA targeted gold nanoparticles (AuNPs-PEG$_{2k}$/PSMA-1) with core size of 5 nm and stabilized with PEG$_{2k}$ were also synthesized.

CY-PSMA-1-Au$_{25}$NCs Characterization

The hydrodynamic size of CY-PSMA-1-Au$_{25}$NCs was characterized by a dynamic light scattering system (DynoPro NanoStar). For absolute size determination, transmission electron microscope (FEI Tecnai F300 kV) was used. Samples were prepared by putting one drop of sample onto 400 mesh formvar/carbon supported copper grids (Ted Pella, Inc.), and dried naturally at room temperature. Absorbance of CY-PSMA-1 peptides, excitation and emission spectra of nanoclusters were recorded with Tecan Infinite M200 plate reader. The CY-PSMA-1-Au$_{25}$NCs were also tested with UV-vis spectrometer (Lambda35, Perkin-Elemer). The structure of the nanoclusters were further characterized by high-resolution matrix-assisted laser desorption/ionization mass (MALDI-MS) spectra from an Applied Biosystem 4800 MALDI TOF/TOF Analyzer in a linear model with a-Cyano-4-hydroxycinnamic acid (CHCA) as the matrix. The stability of CY-PSMA-1-Au$_{25}$NCs in serum was examined with a gel electrophoresis assay. The nanoclusters were incubated with 10% fetal bovine serum (FBS) stained with coomassie brilliant blue (CBB) at 37° C. for 30 min. The mixture and CY-PSMA-1-Au$_{25}$NCs alone were both run with 1% agarose gel and 1×TAE running buffer at 120 kV. Each chamber was loaded with 10 µL nanoclusters, 5 µL of glycerol, and 5 µL of 4×TAE.

Cell Internalization and Uptake Quantification

Retrovirally transformed PSMA-positive PC3pip cells and transfection control PC3flu cells were obtained from Dr. Michel Sadelain in 2000 (Laboratory of Gene Transfer and Gene Expression, Gene Transfer and Somatic Cell Engineering Facility, Memorial-Sloan Kettering Cancer Center, New York, N.Y.). PC3pip and PC3flu cells were cultured in RPMI1640 medium with 2 mmol/L L-glutamine and 10% FBS at 37° C. and 5% CO$_2$. PC3pip and PC3flu cells were seeded in 8-well plates at 2000 cells per well and allowed to grow until about 70% confluency. The CY-PSMA-1-Au$_{25}$NCs were added to each well at an Au concentration of 30 µg/ml, and co-incubated for 24 h. Next, the media were removed and the cells were washed three times with PBS and then fixed with 4% paraformaldehyde for 10 min. The cell were then washed and stained with DAPI to visualize the nuclei and observed under a Leica HyVolution SP8 confocal microscope (Leica Microsystem Inc.).

To quantify CY-PSMA-1-Au$_{25}$NCs uptake by PC3pip and PC3flu cells, both cell lines were seeded in 6-well plates at 1×10$^5$ cells per well and cultured for 24 h. The nanoclusters were added to each well at Au concentration of 60 µg/ml, and incubated for 24. The media were removed and the cells were washed three times with PBS. Next, the cells from each well were trypsinized, centrifuged, washed with PBS, counted and collected in 1.5 ml Eppendorf tubes. 0.5 mL aqua regia was added to each tube to digest the cells overnight. Each sample was then diluted with DI water. Au concentration in each sample was measured by ICP-OES (Agilent technologies, 700 series).

Competition Binding Assay

LNcap cells were trypsinized and washed with cold Tris buffer (0.5 mM). Cell suspensions were divided in Eppendorf tubes (5×10$^5$ cells in each tube) and incubated with ZJ24, CY-PSMA-1, and CY-PSMA-1-Au$_{25}$NCs at different concentrations in the presence of 12 nmol/L N—[N—[(S)-1,3-dicarboxypropyl]carbamoyl]-S-[3H]-methyl-L-cysteine ($^3$H-ZJ24, GE Healthcare Life Sciences) in 300 µL Tri buffer for 1 h at 37° C. Each group was done in triplicate. The mixture was then centrifuged and washed three times with cold PBS. Finally, 4 m L of EcoLume cocktail (MP biomedicals) was added to each sample, and radioactivity was counted by a scintillation counter. The concentration of ligands required to inhibit 50% of binding (IC$_{50}$) was determined by GraphPad Prism 3.0.

Intracellular ROS Detection

PC3pip and PC3flu cells were seeded in 96-well plates and incubated with CY-PSMA-1-Au$_{25}$NCs at 60 µg/ml for 24 h. Cells without addition of NCs were used as a control. After incubation the medium was removed and cells were washed with PBS. 20 µM DCFDA agent in HEPES buffer was added to each well and incubated for another 30 min. Cells were then washed with PBS and radiated at 6 Gy. The fluorescence intensity for each well was measured by a plate reader at Ex/Em (nm) of 495/525. Cells without radiation were also measured as background.

In Vitro Radiosensitization Evaluation

PC3pip and PC3flu cells were seeded in 6-well plate at 1×10$^5$ cells per well and incubated overnight. CY-PSMA-1-Au$_{25}$NCs were then added to the cells at an Au concentration of 60 µg/ml. Cells without any particles added were used as a control. Following incubation for 24 h, the media were removed and cells were washed with PBS to remove the non-internalized nanoclusters. The cells were then irradiated with X-ray at doses of 0, 2, 4, 6 and 8 Gy. All treatments were carried out only once. Next, the cells were trypsinized, counted, and seeded into 6-well plates. After incubating for 10 days, the colonies formed were washed with PBS and fixed with 4% paraformaldehyde. 0.4% crystal violet solution in PBS was added to stain the colonies. The colony number was then counted to calculate the surviving fraction.

Animals and Tumor Xenograft Models

All animal procedures were performed according to Institutional Animal Care and Use Committee (IACUA)-approved protocols. Nude mice with flank tumors, PC3pip tumor at the right side and PC3flu tumor at the left side, were used to evaluate the radiotherapy effect of PSMA-targeted AuNPs. PC3pip or PC3flu cells were prepared and suspended in PBS/matrigel at 1×10$^7$ cells/ml. The nude mice were anesthetized under isoflurane and inoculated with 100 µl cell suspension subcutaneously. Animals were observed every other day until tumors achieved a size of around 100 mm$^3$, at which point the study was initiated.

In Vivo CT Imaging

Mice bearing PC3pip and PC3flu tumors were randomly picked and intravenously injected with CY-PSMA-1-Au$_{25}$NCs and PSMA-targeted 5 nm AuNPs at a dose of 5 mg Au/kg. The mice were anesthetized under isoflurane and scanned by a preclinical Siemens Inveon Positron Emission Tomography-Computed Tomography system before intravenous injection of nanoclusters and at 0.5 h, 1 h, 2 h, 4 h, 6 h, and 24 h after administration of the clusters. The CT scanning was performed at a tube voltage of 70 kV, current of 300 μA, and gantry rotation time of 140 ms. CT images were reconstructed and the Hounsfield unit (HU) was quantified at the tumor areas.

Biodistribution

At 4 h and 24 h post injection of CY-PSMA-1-Au$_{25}$NCs, the mice were sacrificed after the last CT scanning. PC3pip and PC3flu tumors and organs, including liver, spleen, heart, lung, kidneys, and urine, were discretized, weighed and lyophilized. The dried samples were then immersed in aqua regia and digested by gently shaking them for 3 days. When all the tissues were completely digested, the aqua regia solution was diluted with DI water and then measured by ICP-MS to determine the Au content. The clearance of Au from the body was directly compared with PSMA-targeted 5 nm AuNPs.

In Vivo Radiation Therapy

When the tumor size reached around 100 mm$^3$, the tumor-bearing mice were picked randomly, and injected with CY-PSMA-1-Au$_{25}$NCs at 30 μg Au/g dose of Au concentration. As a control, mice with PC3pip and PC3flu tumors were also injected with an equal volume of PBS. 4 hours after injection, the mice received 6 Gy of X-ray radiation focused at the tumor area only. The tumor size and body weights of the irradiated mice were monitored every other day for 18 days. Non-irradiated mice injected with PBS or CY-PSMA-1-Au$_{25}$NCs, were also monitored at the same time. The tumor sizes and body weights of mice were recorded every other day.

Statistics

All the experiments were performed in triplicates unless stated otherwise. All values in the results were expressed as mean±SD. Descriptive statistics and significant differences between groups were analyzed using two-tailed student's t-tests.

Results

Figure 7:
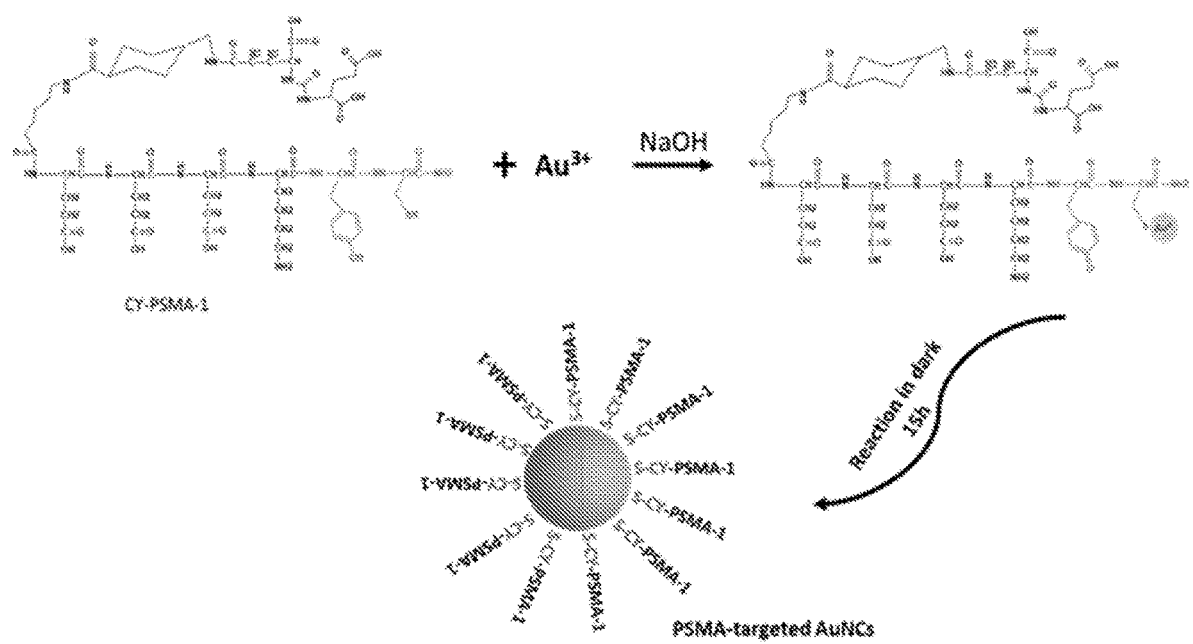
FIG. 7 is a schematic illumination of Au$_{25}$NCs synthesis by CY-PSMA-1 ligand reduction and stabilization. The Cys residue binds to Au$^{3+}$ ions with the thiol group and an increase in pH by NaOH turns the phenolic group of Tyr to into a phenoxide ion, which can reduce the Au$^{3+}$ ions. The reduced Au atoms further aggregate to form gold nanoclusters, which are stabilized by the peptide via the SH groups. Once the pH increased to 12, the added Au$^{3+}$ cations are coordinated to the peptide, reduced to Au$^0$, and the CY-PSMA-1 ligand is thereby covalently bound to the Au$_{25}$NC via the S—Au bond.
Figure 8:
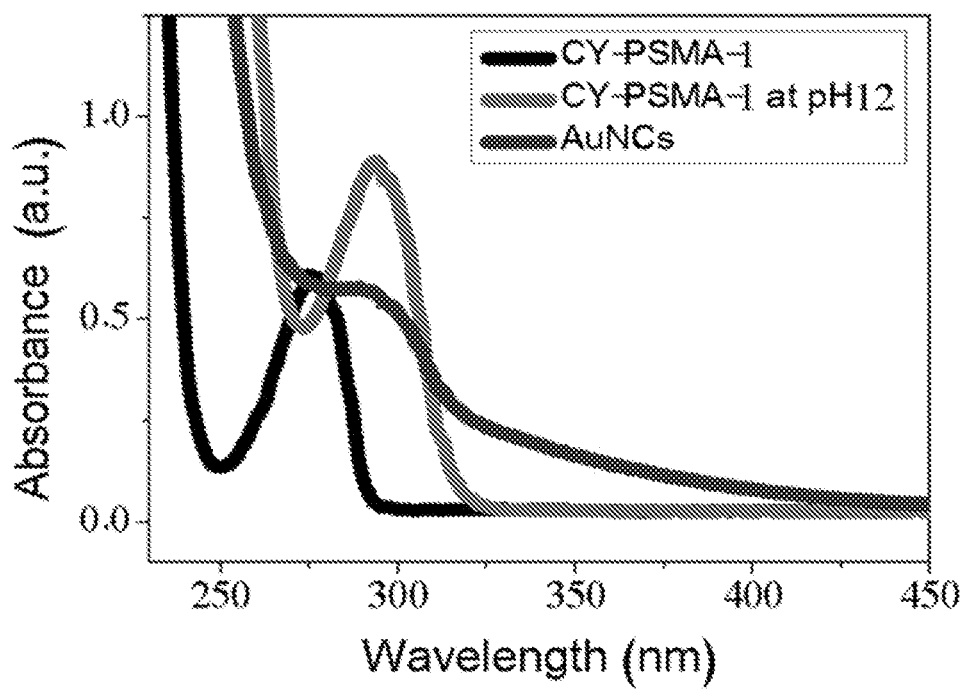
FIG. 8 illustrates absorbance spectra of CY-PSMA-1 and AuNCs in solutions. CY-PSMA-1 (black) has an absorbance peak at 274 nm, which shifts to 295 nm after addition of NaOH to raise the pH to 12 (red). The peak shift as a function of pH was due to the transformation of phenol to phenoxide. The absorbance of any formed AuNCs can be monitored with the peak rising at 295 nm (blue).
Figure 9:
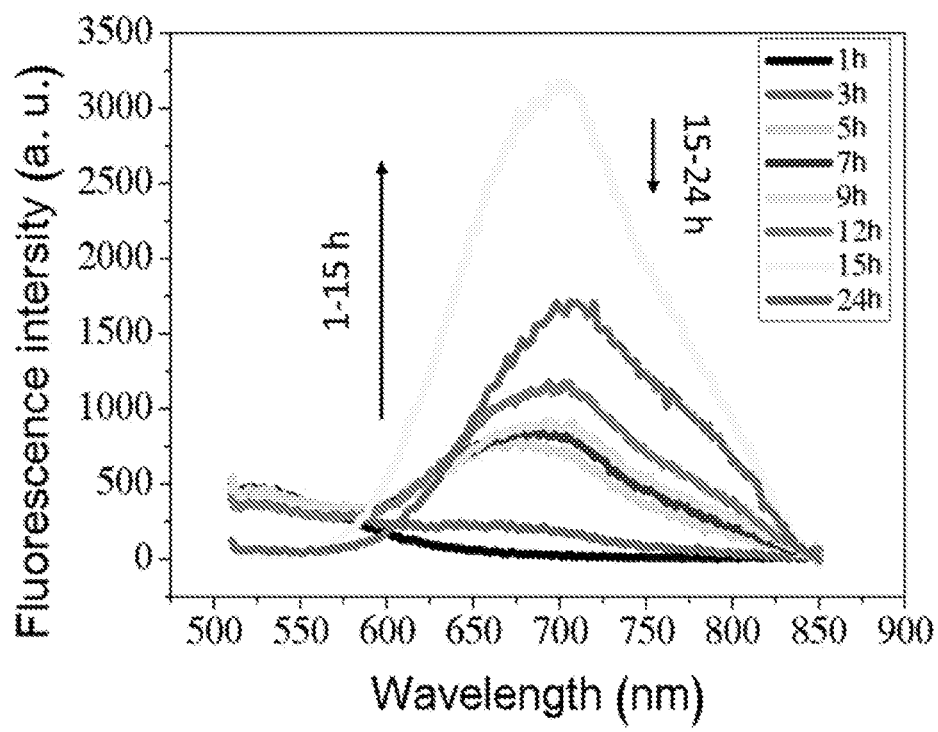
FIG. 9 illustrates the emission spectra of the reaction mixture indicating the formation of $Au_{25}NCs$ over time. The fluorescence intensity at 700 nm increased as a function of reacting time, and peaked after 15 h.
Figure 10:
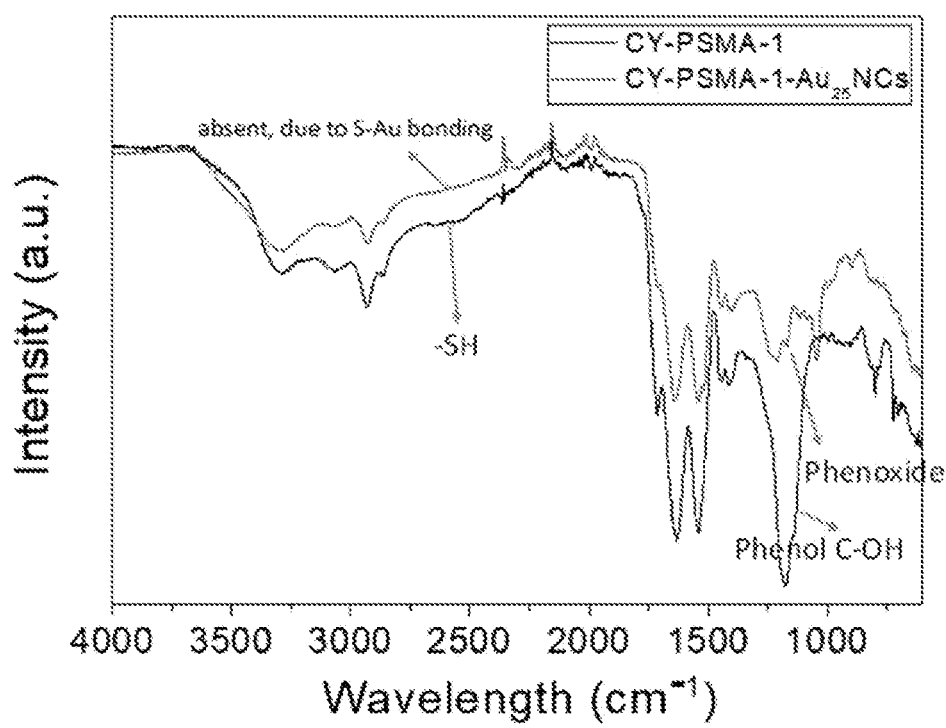
FIG. 10 illustrates FTIR spectra of CY-PSMA-1 and PSMA-targeted AuNCs. The band at 2520 $cm^{-1}$ has been assigned to the stretching vibration of the —SH group (black). After reacting with Au, the IR absorbance at 2520 $cm^{-1}$ decreased, implicating S—Au bond formation. The band at 1200 $cm^{-1}$ also greatly reduced during the reaction, due to the transformation of phenol to phenoxide.

We have developed a high-affinity ligand, PSMA-1, for the PSMA receptor, which is over-expressed on most prostate cancers. Using optical imaging fluorophores we have demonstrated its selectivity for the PSMA receptor and its biodistribution in mouse models of prostate cancer. To generate PSMA-targeted Au$_{25}$NCs, we first re-synthesized the PSMA-1 to include two additional amino acids. The new ligand, CY-PSMA-1, retained high affinity for the PSMA expressing cells and contained additional Cys and Tyr residues to enable reduction and capping of the nanoclusters (NCs), which was the foundation for in-situ Au$_{25}$NC formation (FIGS. 7-9). The ligand was combined at pH 12 with Au$^{3+}$ ions resulting in the formation of Au$_{25}$NCs. The nanoclusters formed were examined with TEM and showed that the PSMA-targeted Au$_{25}$NCs have a narrow size distribution with an average diameter of 1.5 nm (FIG. 2*a*), and a hydrodynamic diameter of 3.0 nm (FIG. 2*b*). The CY-PSMA-1-Au$_{25}$NCs exhibited an excitation peak at 490 nm and emission peak at 700 nm (FIG. 2*c*). Fourier-transform infrared spectroscopy (FTIR) confirmed the presence of CY-PSMA-1 and S—Au bonding (FIG. 10). Further characterization using MALDI-TOF MS confirmed AuNCs consisting of 25 Au atoms, which are known to be highly stable (FIG. 2*d*). We next tested if the CY-PSMA-1-Au$_{25}$NC had good stability under physiological conditions. After incubation with 10% FBS solution at 37° C. for 30 min, the complex was analyzed using gel electrophoresis showing that there was no detectable serum adsorption to the Au$_{25}$NCs.

Our first step in evaluating the utility of these targeted-NC was to measure uptake in vitro. PSMA receptor positive, PC3pip, or PSMA-receptor negative, PC3flu, cells were incubated with CY-PSMA-1-Au$_{25}$NCs. Confocal fluorescence imaging of the cells showed that the PC3pip cells bind and take up the nanoclusters more avidly than the receptor-negative PC3flu cells (FIG. 3*a*). ICP-MS measurements of the gold content in each set of cells showed that PC3pip cells had almost a 2-fold higher Au content than the PC3flu cells (FIG. 3*b*), suggesting that targeting the Au$_{25}$NC to PSMA receptor doubles uptake. We next measured binding of the targeted-NCs to cells using a competition binding assay. PSMA-expressing LNcap cells were incubated with CY-PSMA-1, CY-PSMA-1-Au$_{25}$NCs and the parent ligand ZJ24 at various concentrations in the presence of 12 nM $^3$H-labelled ZJ24 ligand. The cell uptake associated radioactivity was measured via a scintillation counter. Compared to ZJ24 (IC$_{50}$=8.31 nM) and CY-PSMA-1 (IC$_{50}$=1.69 nM) ligands, the PSMA-targeted Au$_{25}$NCs exhibited a remarkably lower IC$_{50}$ value (IC$_{50}$=0.09 nM), indicating an excellent targeting affinity likely due to avidity effects (FIG. 3*c*).

Our next in vitro study was to determine if the targeted-NCs could serve to improve radiotherapy. Because the mechanism of radiosensitization by gold is reactive oxygen species (ROS) generation initiated by electron ejection from gold that is irradiated with X-rays, we first tested to see if irradiated gold nanoclusters would generate ROS using a DCFDA assay. DCFDA is a non-fluorescent molecule that coverts to fluorescent DCP upon exposure to ROS. PC3pip and PC3flu cells were incubated with targeted-Au$_{25}$NCs for 24 hours and then irradiated (6 Gy), FIG. 3*d*. PC3pip cells generated much more DCFDA conversion and fluorescence of DCP than did PC3flu cells, indicating successful ROS production. To see if ROS generation converted to increase cellular toxicity, in vitro radiation sensitization was measured using a colony survival assay. According to the cell survival fraction curves (FIG. 3*e*), radiation sensitivity was enhanced for PC3pip cells incubated with PSMA-targeted Au$_{25}$NCs compared to PC3flu or control cells not incubated with any Au$_{25}$NCs. By fitting the survival curves to a multitarget single-hit model, the sensitization enhancement ratios (SER) of PSMA-targeted Au$_{25}$NCs for PC3pip and PC3flu cells were determined to be 2.1 and 1.4, respectively. This suggests that actively targeting of Au$_{25}$NCs to PC3pip cells can significantly enhance the radiation sensitivity.

Next, we performed in vivo experiments to evaluate the tumor targeting ability and clearance of CY-PSMA-1-Au$_{25}$NCs. The ultrasmall size of the targeted-Au$_{25}$NCs is especially attractive for in vivo tumor theranostics already benefiting from the passive tumor targeting ability and high renal clearance rate for such small clusters. We established a prostate tumor model, where both PSMA-positive and PSMA-negative tumors were implanted on the flanks of the same mouse and then used X-ray computed tomography (CT) to monitor specific Au accumulation within the tumors and in the bladder. Following a pre-injection scan, CY-PSMA-1-Au$_{25}$NCs were injected into the tail vein of the animals and CT scans were carried out at 0.5 h, 1 h, 2 h, 4 h, 6 h, and 24 h post-injection. Reconstruction of the 3D X-ray CT images showed increased CY-PSMA-1-Au$_{25}$NC in the PSMA-overexpressing PC3pip tumors as early as 1 hour after injection, peaking at 4 hours after injection, and clearance of the nanoclusters by 24 hours. In contrast, the PC3flu tumor showed almost no signal enhancement even at 4 hours post injection (FIG. 4*a*, indicated by green circles). The CT signal is a direct reflection of the local Au atom concentration. The corresponding CT values at tumor sites were plotted in FIG. 4*b* showing that in PC3pip tumors the Au$_{25}$NC content reached 374 Hounsfield unit (HU) at 4 h, compared to 195 HU monitored at the PC3flu tumor, the only difference being the active targeting of targeted-Au$_{25}$NCs via the PSMA antigen. Importantly, the bladder could be clearly identified in the 3D CT images (indicated by red circles) 30 min post injection with bladder accumulation peaking at 4 h after injection (FIG. 4c). This suggests that fast renal clearance eliminates the CY-PSMA-1-Au$_{25}$NCs from the animals within hours.

To further understand the in vivo behavior of CY-PSMA-1-Au$_{25}$NC, we analyzed Au biodistribution at 4 h and 24 h post injection using ICP-MS. As shown in FIG. 4d, the Au amount in PC3pip tumor was 2.9 and 2.2 times of that in the PC3flu tumor at 4 h and 24 h, respectively. This shows that targeting the PSMA receptor overexpressed on prostate cancer cells (PC3pip) provides greater accumulation of the targeted NCs than would occur by passive accumulation through the enhanced permeability and retention (EPR) effect. Due to the fast clearance of the NCs, the untargeted AuNCs have a low accumulation in PSMA-lacking tumors with 2% of injected dose (ID/g) in contrast to the targeted Au$_{25}$NCs that showed a high accumulation in PC3pip tumors with 8.9% ID/g at 4 h post injection. This is greater than that achieved for RGD-targeted nanoclusters, which reached 6.4% ID/g in 4T1 tumors after 4 h. Moreover, the Au content in the liver is less than 3% ID/g, which is much lower compared to a study by Tsvirkun et al. using 10 nm 30 nm and 100 nm gold nanoparticles. The Au content in urine was significantly higher than in other organs.

Figure 11A:
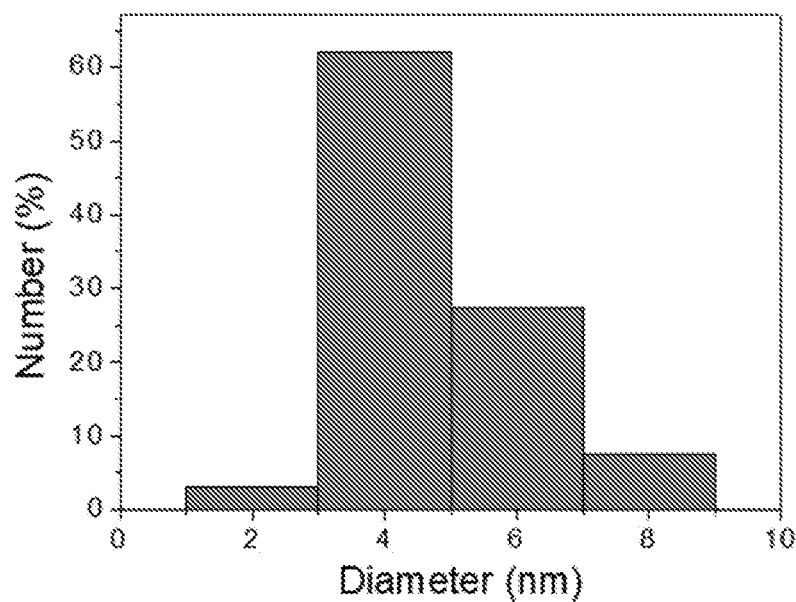
FIGS. 11(A-B) illustrates the distribution of core diameters of $AuNPs-PEG_{2K}/PSMA-1$ obtained by TEM. Inset shows a TEM image AuNPs (scale bar 50 nm). Distribution of the hydrodynamic diameters of $AuNPs-PEG_{2K}/PSMA-1$ obtained by DLS.
Figure 11B:
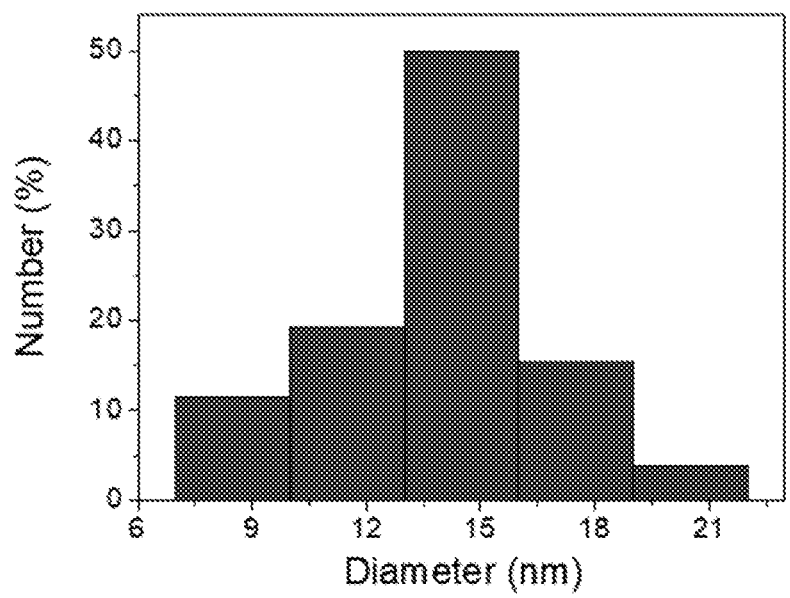

To determine the critical size effect on clearance, we also synthesized PSMA-targeted AuNPs, which had a core size of 5 nm and hydrodynamic size of 14 nm (FIG. 11). Injected at the same dose for gold, the PSMA-targeted AuNPs had about 2 times more Au accumulation in liver compared to Au$_{25}$NCs and only 0.9% ID/g in urine at 24 h post injection (FIG. 5a), indicating the AuNPs were unable to be cleared via urine. CT images of the digestive systems of mice at 24 h post injection also confirmed less accumulation of CY-PSMA-1-Au$_{25}$NCs in the gut than the 5 nm PSMA-targeted AuNPs (FIG. 5b, c). Presumably, since the CY-PSMA-1-Au$_{25}$NCs are smaller than the glomerular filtration cutoff, they escape capture by the reticuloendothelial system (RES) and are excreted via the urinary system, limiting potential toxicity to the RES organs. PSMA-targeted AuNPs with a size bigger than the renal-clearance threshold are slower or unable to be excreted from the kidney and will be cleared via the RES and digestion systems. The biodistribution results were consistent with the CT images, confirming that PSMA-targeted Au$_{25}$NCs can be targeted to the PSMA-receptors expressed in tumors and also preferentially undergo renal clearance.

Highly encouraged by the excellent in vitro and in vivo tumor targeting of the CY-PSMA-1-Au$_{25}$NCs, we investigated the potential use of these agents as radiosensitizers for prostate tumor radiation therapy. Nude mice bearing both PC3pip and PC3flu tumors were divided into four treatment groups: (a) PBS injection only; (b) PBS injection with X-ray radiation; (c) CY-PSMA-1-Au$_{25}$NCs injection only; (d) CY-PSMA-1-Au$_{25}$NCs injection with X-ray radiation. Where indicated, a radiation dose of 6 Gy was given to each animal group 4 hours after injection of the sensitizer to take advantage of the peak accumulation in the tumor, FIG. 4b. The tumor sizes and body weights of the studied mice were monitored over 18 days (FIG. 6). Mice irradiated after injection with CY-PSMA-1-Au$_{25}$NCs showed a significant decrease in the rate of tumor growth and kept a more stable body weight. Compared to the PBS controls, the CY-PSMA-1-Au$_{25}$NCs also enhanced the sensitivity of PC3flu tumors to irradiation. However, this occurred to a significantly lesser extent than for the PC3pip cells (FIG. 6) and is likely due to passive EPR accumulation. In mice that only received CY-PSMA-1-Au$_{25}$NCs but no X-ray treatment, the PC3pip and PC3flu tumors shared similar growth kinetics and their growth was comparable to the mice injected with PBS only. Irradiation in the presence of targeted NCs stabilized the body weight of the animals which otherwise decreased significantly if the animals were not irradiated, dropping by 19%. A similar observation was made for the body weights of PBS-administered mice with/without radiation. Clearly, radiotherapy sensitized by PSMA-targeted Au$_{25}$NCs enhanced the tumor growth inhibition and therapeutic outcome, as evidenced by the stabilized body weights.

In summary, this work demonstrates the synthesis and selective targeting of gold nanoclusters to prostate cancer cells that express the targeted biomarker. We developed a target-specific sensitizer for prostate cancer radiation therapy based on the prostate-specific membrane antigen (PSMA) targeting ligand, CY-PSMA-1. The targeting peptide had a high affinity to PSMA-expressing cancer cells, indicating that the additional Try and Cys residues in the ligand, necessary for the formation of the PSMA-targeted radiosensitizing Au$_{25}$NCs, did not alter the affinity of the ligand. The targeted gold nanoclusters demonstrated higher PSMA affinity than the CY-PSMA-1 alone and were rapidly taken up by prostate tumors to approximately 9% ID/g tissue, while, at the same time, being quickly renally excreted. Compared to PSMA-targeted 5 nm gold nanoparticles there was much lower liver uptake as well. Targeting is selective for PSMA-receptor expressing prostate cancer cells, more efficient compared to a passive EPR-driven therapy approach, and significantly improved the radiation therapy of tumors in mice. This approach significantly enhances the successful outcome of radiation therapy. With high prostate cancer targeting specificity and fast renal clearance, the presented CY-PSMA-1-Au$_{25}$NCs is the most effective gold-based radiosensitizers for prostate cancer therapy known today.

All references cited herein, including patents, patent applications, papers, text books, and the like, and the references cited therein, to the extent that they are not already, are hereby incorporated herein by reference in their entirety. The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

Having described the invention, we claim:

1. A composition for detecting and/or treating cancer, the composition comprising a plurality of compounds that include formula (I):

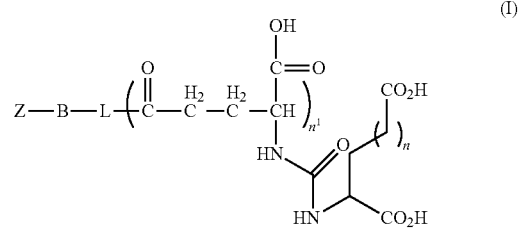

wherein:

n and $n^1$ are each independently 1, 2, 3, or 4;

L is an optionally substituted aliphatic or heteroaliphatic linking group;

B comprises at least one negatively charged amino acid; and

Z has the formula

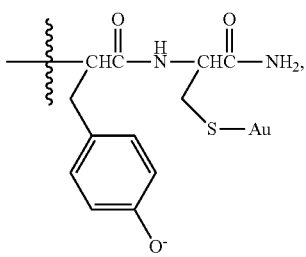

wherein Z is directly or indirectly linked to B.

2. The composition of claim 1, wherein B has the following formula:

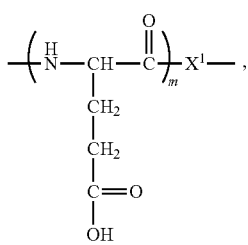

wherein m is 1, 2, 3, or 4, $X^1$ is an amino acid, and wherein Z is directly or indirectly linked to $X^1$.

3. The composition of claim 1, wherein B has the following formula:

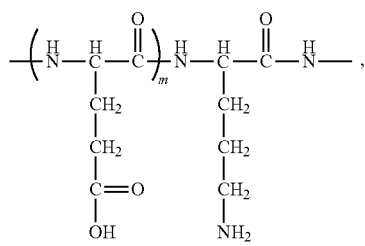

wherein m is 1, 2, 3, or 4.

4. The composition of claim 1, wherein L includes at least one ring selected from the group consisting of an optionally substituted 4 to 7 membered nonaromatic heterocyclic ring and an optionally substituted C4-C7 cycloalkyl ring.

5. The composition of claim 1, comprising the formula (II):

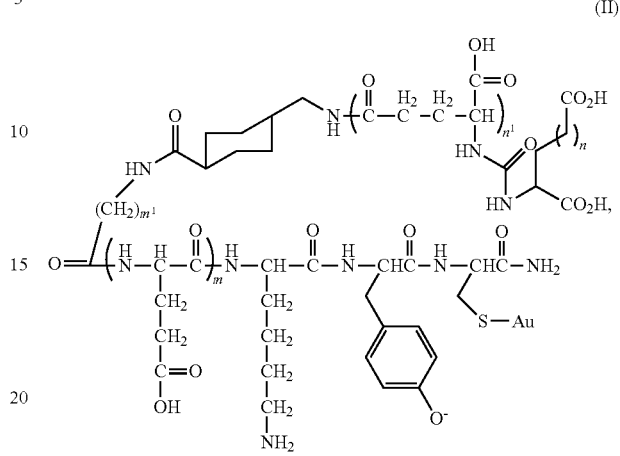

wherein m, n, and $n^1$ are each independently 1, 2, 3, or 4, and wherein $m^1$ is 3-7.

6. The composition of claim 1, wherein the plurality of compounds has formed gold nanoclusters.

7. The composition of claim 6, the gold nanoclusters including 10-150 gold atoms.

8. The composition of claim 6, the gold nanoclusters including 10-40 gold atoms.

9. The composition of claim 6, wherein the gold nanoclusters are less than about 10 nm in diameter.

10. The composition of claim 6, wherein the cancer is a PSMA expressing cancer selected from glioma, retinoblastoma, lung cancer, melanoma, breast cancer, ovarian cancer, endometrial cancer, and prostate cancer.

11. The composition of claim 6, wherein the cancer is prostate cancer.

12. A method for treating prostate cancer comprising:

(a) administering systemically to a subject with prostate cancer a therapeutically effective amount of a composition, the composition comprising a gold nanocluster, the gold nanocluster including a plurality of compounds having formula (I):

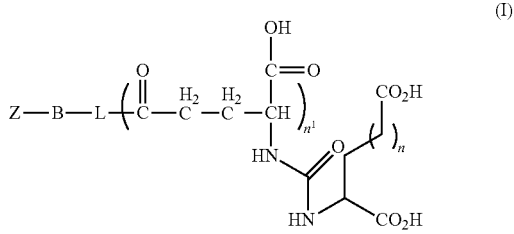

wherein n and $n^1$ are each independently 1, 2, 3, or 4, L is an optionally substituted aliphatic or heteroaliphatic linking group, B comprises at least one negatively charged amino acid, and Z has the formula

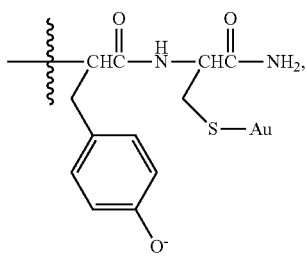

wherein Z is directly or indirectly linked to B; and (b) irradiating the prostate cancer of the subject, thereby inducing the radiosensitizing effects of the gold nanocluster.

13. The method of claim 12, further comprising the step of detecting the gold nanocluster selectively targeted to prostate cancer cells of the subject to determine the location and/or distribution of the prostate cancer cells in the subject.

14. The method of claim 13, wherein the presence of the gold nanocluster is detected in the subject by at least one positron emission tomography (PET) imaging or computer tomography (CT) imaging.

15. The method of claim 12, wherein the composition is administered by intravenous injection.

16. The method of claim 12, wherein B has the following formula:

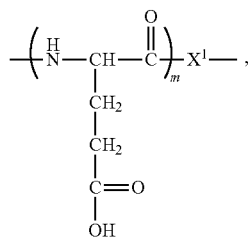

wherein m is 1, 2, 3, or 4, $X^1$ is an amino acid, and wherein Z is directly or indirectly linked to $X^1$.

17. The method of claim 12, wherein B has the following formula:

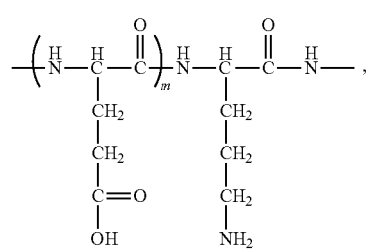

wherein m is 1, 2, 3, or 4.

18. The method of claim 12, wherein L includes at least one ring selected from the group consisting of an optionally substituted 4 to 7 membered nonaromatic heterocyclic ring and an optionally substituted C4-C7 cycloalkyl ring.

19. The method of claim 12, the compounds comprising the formula (II):

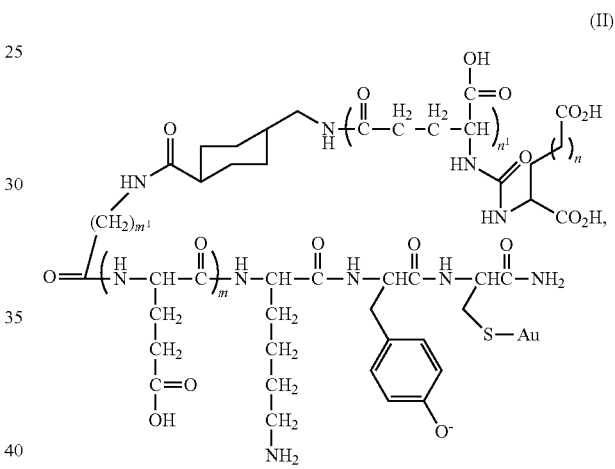

wherein m, n, and $n^1$ are each independently 1, 2, 3, or 4, and wherein $m^1$ is 3-7.

20. The method of claim 12, wherein the gold nanocluster includes about 10 to about 150 gold atoms.

21. The method of claim 12, wherein the gold nanocluster includes about 10 to about 40 gold atoms.

22. The composition of claim 12, wherein the gold nanocluster is less than about 10 nm in diameter.

23. The composition of claim 12, wherein the prostate cancer is irradiated with X-ray radiation.

24. The composition of claim 12, wherein the prostate cancer is irradiated with gamma ray radiation.

* * * * *